US008143429B2

(12) United States Patent
Ochiai et al.

(10) Patent No.: US 8,143,429 B2
(45) Date of Patent: Mar. 27, 2012

(54) PROCESS FOR PRODUCING ORGANIC TRANSITION METAL COMPLEX COMPOUND, METATHESIS CATALYST PRODUCED BY USING THE SAME, RING-OPENING METATHESIS POLYMER OBTAINABLE WITH THE METATHESIS CATALYST, AND PROCESS FOR PRODUCING THE POLYMER

(75) Inventors: Takashi Ochiai, Chiba (JP); Yuichi Okawa, Ichihara (JP); Tadahiro Sunaga, Yamato (JP)

(73) Assignee: Mitsui Chemicals, Inc., Minato-Ku, Tokyo (JP)

( * ) Notice: Subject to any disclaimer, the term of this patent is extended or adjusted under 35 U.S.C. 154(b) by 821 days.

(21) Appl. No.: 12/090,830

(22) PCT Filed: Oct. 17, 2006

(86) PCT No.: PCT/JP2006/320613
§ 371 (c)(1),
(2), (4) Date: Apr. 18, 2008

(87) PCT Pub. No.: WO2007/046352
PCT Pub. Date: Apr. 26, 2007

(65) Prior Publication Data
US 2009/0124772 A1 May 14, 2009

(30) Foreign Application Priority Data
Oct. 20, 2005 (JP) ................................. 2005-306026

(51) Int. Cl.
C07F 11/00 (2006.01)
C08F 4/69 (2006.01)
C08G 61/08 (2006.01)
(52) U.S. Cl. .............. 556/43; 556/46; 556/58; 556/136; 556/137; 526/170; 526/171; 526/281
(58) Field of Classification Search .................. 526/170, 526/281, 171; 556/58, 43, 46, 136, 137
See application file for complete search history.

(56) References Cited

U.S. PATENT DOCUMENTS

| 4,727,215 A * | 2/1988 | Schrock .................. 554/161 |
| 5,597,935 A | 1/1997 | Jordan et al. | |
| 5,917,071 A * | 6/1999 | Grubbs et al. .................. 556/21 |
| 2005/0119412 A1 * | 6/2005 | Okawa et al. .................. 525/211 |

FOREIGN PATENT DOCUMENTS

| EP | 0 796 607 A2 | 9/1997 |
| JP | 7-258390 A | 10/1995 |
| WO | WO 95/32979 A1 | 12/1995 |

OTHER PUBLICATIONS

Form PCT/ISA/210 (International Search Report) dated Nov. 21, 2006.

Amritanshu Sinha et al., "Reactions of Mo(NAr)(Ch-t-Bu)(CH₂-t-Bu)₂ With Alcohols to Give Metathesis Catalysts of the Type Mo(NAr)(Ch-t-Bu)(CH₂-t-Bu)(OR)", Organometallics, Apr. 12, 2004, vol. 23, No. 8, pp. 1643-1645, American Chemical Society (cited in the International Search Report).
Lourdes Pia H, Lopez et al., "Formation of Dimers That Contain Unbridged W(IV)W/(IV) Double Bonds", Journal of the American Chemical Society, Aug. 11, 2004, vol. 126, No. 31, pp. 9526-9527 (cited in the International Search Report).
Guy Schoettel et al., "A Simple Route to Molybdenum-Carbene Catalysts for Alkene Metathesis", Chemical Communications, Journal of the Chemical Society, Aug. 1, 1989, vol. 15, pp. 1062-1063 (cited in the International Search Report).
Gary M. Diamond et al., "Synthesis of Group 4 Metal rac-(EBI)M(NR₂)₂ Complexes by Amine Elimination. Scope and Limitations", Organometallics, 1996, vol. 15, pp. 4030-4037, American Chemical Society (cited on p. 5 of the specification).
Richard R. Schrock, "Living Ring-Opening Metathesis Polymerization Catalyzed by Well-Characterized Transition-Metal Alkylidene Complexes", Acc. Chem. Res., 1990, vol. 23, pp. 158-165, American Chemical Society (cited on p. 5 of the specification).
R. R. Schrock et al., "Further Studies of Imido Alkylidene Complexes of Tungsten, Well-Characterized Olefin Metathesis Catalysts With Controllable Activity", Organometallics, 1990, vol. 9, pp. 2262-2275, American Chemical Society (cited on p. 5 of the specification).
Richard R. Schrock, et al. "Synthesis of Molybdenum Imido Alkylidene Complexes and Some Reactions Involving Acyclic Olefins", J. Am. Chem, Soc., 1990, vol. 112, pp. 3875-3886, American Chemical Society (cited on pp. 5-6 of the specification).
Richard R. Schrock et al., "*Molybdenum and Tungsten Imido Alkylidene Complexes as Efficient Olefin-Metathesis Catalysts*", Angew Chem. Int. Ed., 2003, pp. 4592-4633.
Office Action from Chinese Patent Office issued in Applicant's corresponding Chinese Patent Application No. 200680038690.3 dated Jun. 28, 2010.
A.M. Lapointe, et al.: "Alkyl, alkylidene, and alkylidyne complexes of rhenium", Organometallics, 1995, pp. 1875-1884, XP002596520.
E. Bleuel, et al.: "Synthesis and molecular structure of four-coordinate neutral and cationic diphenylcarbenerhodium(I) complexes", Journal of Organometallic Chemistry, vol. 617-618, 2001, pp. 502-510, XP002596521.
Extended European Search Report issued in corresponding European Patent Application No. 06 81 1868 dated Jan. 13, 2011.

* cited by examiner

*Primary Examiner* — Fred M Teskin
(74) *Attorney, Agent, or Firm* — Buchanan Ingersoll & Rooney PC

(57) ABSTRACT

A process for synthesizing an organic transition metal complex compound with an atom group having an electron-donor ability, in an industrially and economically advantageous manner, without a compound having a proton-donor ability being a metal salt, and a metathesis catalyst produced with the use of the above process, are provided. A process for producing an organic transition metal complex compound in which an atom group having an electron-withdrawing ability can be converted into an atom group having a stronger electron-donor ability, by contacting an compound having a proton-donor ability with the organic transition metal complex compound with an atom group having an electron-withdrawing ability, in the presence of an basic compound, and a metathesis catalyst of which the content of an alkali metal is reduced, and which is obtainable with the use of the above process, are provided.

3 Claims, 1 Drawing Sheet

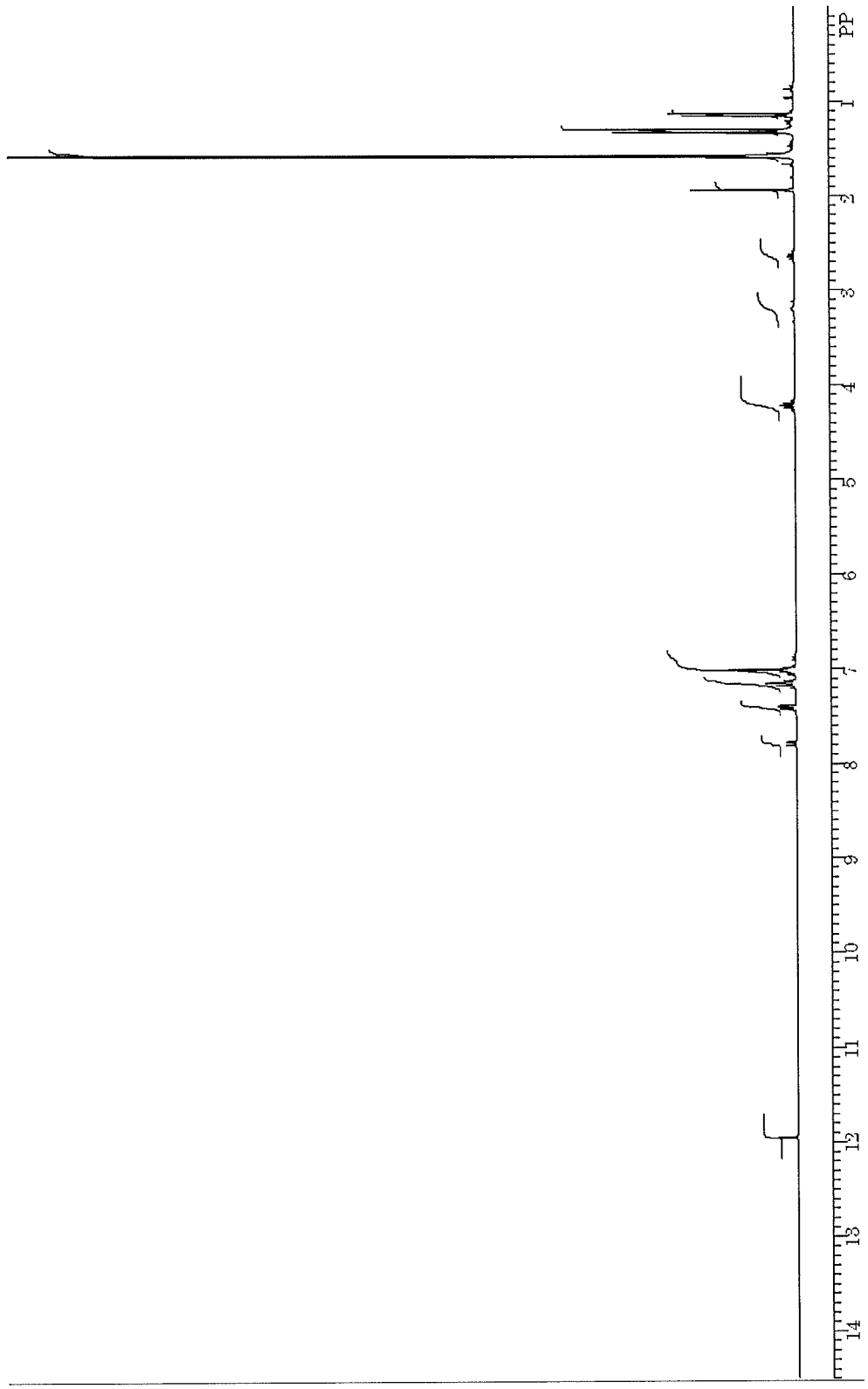

PROCESS FOR PRODUCING ORGANIC TRANSITION METAL COMPLEX COMPOUND, METATHESIS CATALYST PRODUCED BY USING THE SAME, RING-OPENING METATHESIS POLYMER OBTAINABLE WITH THE METATHESIS CATALYST, AND PROCESS FOR PRODUCING THE POLYMER

TECHNICAL FIELD

The present invention relates to a process for producing an organic transition metal complex compound, a metathesis catalyst produced by using the same, a ring-opening metathesis polymer obtainable by polymerizing with the metathesis catalyst, and a process for producing the polymer.

BACKGROUND ART

Generally, organic transition metal complex compounds tend to be influenced by oxygen, water, and compounds having a proton-donor ability. Some kinds of organic transition metal complex compounds decompose by oxidative decomposition, hydrolysis, or elimination decomposition or the like, when being in contact with oxygen, water, or a compound having a proton-donor ability.

In order to synthesize an organic transition metal complex compound with an atom group having a strong electron-donor ability, such as cyclopentadienyl, alkoxy, and carboxyl, a reactant with an atom group having a stronger electron-donor ability is used in many cases, the reactant being made by converting a compound having a proton-donor ability to an alkyl alkali metal salt which has no proton-donor ability. When an organic transition metal complex compound is produced by using this process, however, a desired portion of an organic transition metal complex compound does not react with the alkyl alkali metal salt due to the strong cationic property of the alkali metal, therefore the organic transition metal complex compound may decompose or a side reaction may occur, resulting in a desired organic transition metal complex compound not being obtained in some cases. In addition, since the reactivity of a ligand exchange vary depending on kinds of an alkali metal ion and an atom group having a counter anion, organic transition metal complex compounds which can be produced are restricted. From these reasons, an improved process for producing an organic transition metal complex compound, in which a decomposition reaction or a side reaction never occurs, is needed.

On the other hand, in organic transition metal metallocene complex compounds having a hydrocarbon-based ligand, such as cyclopentadienyl, Jordan et al. have reported a process for synthesizing an organic transition metal metallocene complex compound synthesized by contacting a certain cyclopentadiene having a proton-donor ability with a transition metal dimethylamide compound without the use of alkali metal salt, without a synthetic reaction between a cyclopentadienyl metal salt and a transition metal chloride being carried out in which the cyclopentadienyl metal salt is obtained by a reaction between cyclopentadiene and an organic metal compound, such as butyllithium, or an hydrogenated alkali metal compound, the process being used in a conventional method. In the synthesis method, a side reaction which may occur in the process where an organic transition metal metallocene complex compound is synthesized by using an alkali metal salt, can be prevented; however, the synthesis reaction needs reaction-conditions of high-temperature and long-period, resulting in an increased production cost (see Patent Documents 1 and 2, and Nonpatent Document 1).

Schrock et al. have recently reported that various metathesis reactions including a ring-opening metathesis polymerization can be driven by using a metathesis catalyst of which central metal is tungsten or molybdenum (see Nonpatent Documents 2, 3 and 4). These metathesis catalysts are organic transition metal alkylidene complex compounds with an atom group having a stronger electron-donor ability, such as alkoxy. The metathesis catalyst is synthesized by contacting an alkyl alkali metal salt obtained by contacting a compound having a proton-donor ability, such as alcohol, with sodium, lithium, potassium, or a metal hydride compound thereof, further with an organic metal compound, such as butyllithium, with an organic transition metal complex compound with a halogen or a triflate, which is an atom group having an electron-withdrawing ability, as a ligand, thereby converting it into an alkoxy or the like having a stronger electron-donor ability. In the process, a halogenated alkali metal or a triflate alkali metal salt is produced as a side product.

Therefore, an excessive alkyl alkali metal salt, which is a reactant, remains in the metathesis catalyst thus-produced. When a metathesis reaction is carried out by using such a metathesis catalyst in which these side products and a reactant remain, a reactive substance may be polymerized with the side products or the reactant being polymerization initiators for an anion polymerization, or the metathesis catalyst may be deteriorated or decomposed with a ligand exchange reaction between the side products or the reactant, and active species in the metathesis reaction occurring, due to the strong ionic property of the side products or the reactant. If metal remains in a product prepared with the use of the metathesis reaction, it may affect the physical properties or the color tone of the product adversely.

In the metathesis polymerization reaction, an unsaturated bond in the main chain is generally converted into a saturated bond by the hydrogenation reaction after polymerization. In the process, when an alkali metal salt derived from the synthesis reaction of a metathesis catalyst, that is, a side product or a reactant, is included in the product, a normal hydrogenation reaction may be impaired by deterioration or decomposition of the side product or the reactant, which is caused by a reaction between the side product or the reactant, and a catalyst for the hydrogenation reaction.

Since an alkali metal having a high ionic property is used in the conventional processes for synthesizing a metathesis catalyst, there are various problems, therefore a process for producing a metathesis catalyst without the use of an alkali metal, is needed.

[Patent Document 1] WO 95/32979 pamphlet
[Patent Document 2] U.S. Pat. No. 5,597,935

DESCRIPTION

[Nonpatent Document 1] Gary M. Diamond, and one other, "Synthesis of Group 4 Metal rac-(EBI)M(NR2)2 Complexes by Amine Elimination. Scope and Limitations", Organometallics, 15, 4030-4037 (1996)

[Nonpatent Document 2] Richard R. Schrock, "Living Ring-Opening Metathesis Polymerization Catalyzed by Well-Characterized Transition-Metal Alkylidene Complexes", Acc. Chem. Res., 23, 158 (1990)

[Nonpatent Document 3] R. R. Schrock, and thirteen others, "Further Studies of Imido Alkylidene Complexes of Tungsten, Well-Characterized Olefin Metathesis Catalysts with Controllable", Organometallics, 9, 2262 (1990)

[Nonpatent Document 4] Richard R. Schrock, and five others, "Synthesis of Molybdenum Imido Alkyidene Complexes and Some Reactions Involving Acyclic Olefins", J. Am. Chem. Soc., 112, 3875 (1990)

DISCLOSURE OF THE INVENTION

The present invention is to provide a process for synthesizing an organic transition metal complex compound with an atom group having an electron-donor ability in the presence of a basic compound, in an industrially and economically advantageous manner, without a compound having a proton-donor ability being a metal salt, and a metathesis catalyst produced with the use of the above process, further a ring-opening metathesis polymer obtainable by polymerizing with the use of the metathesis catalyst, and a process for producing the polymer.

As a result of an intensive investigation for solving the above problems, the present inventors have found a new process for producing an organic transition metal complex compound in which any atom group having an electron-withdrawing ability of an organic transition metal complex compound with any atom group having an electron-withdrawing ability is converted into an atom group having an electron-withdrawing ability and a stronger electron-donor ability derived from any compound having a proton-donor ability, by contacting any compound having a proton-donor ability with the organic transition metal complex compound with any atom group having an electron-withdrawing ability in the presence of any basic compound, and a metathesis catalyst of which the content of an alkali metal is reduced, and which is obtainable with the use of the above process, further a ring-opening metathesis polymer obtainable by polymerizing a cyclic olefin with the use of the metathesis catalyst, and a process for producing the polymer. The present invention has been completed based on these findings.

That is, the present invention is:

[1] a process for producing (C) an organic transition metal complex compound including: converting an atom group having an electron-withdrawing ability of (A) an organic transition metal complex compound with an atom group having an electron-withdrawing ability, into an atom group having an electron-withdrawing ability derived from (B) a compound having a proton-donor ability, by contacting (B) the compound having a proton-donor ability with (A) the organic transition metal complex compound with an atom group having an electron-withdrawing ability, in the presence of a basic compound;

[2] the process for producing the organic transition metal complex compound according to [1], wherein (B) the compound having a proton-donor ability is at least one or more selected from an alcohol and a thiol;

[3] the process for producing the organic transition metal complex compound according to [1] or [2], wherein (A) the organic transition metal complex compound with an atom group having an electron-withdrawing ability, has a metal alkylidene or a metal alkylidyne;

[4] a metathesis catalyst obtainable by being synthesized with the use of the process for producing the organic transition metal complex compound according to any one of [1] to [3] and represented by the following general formula (1);

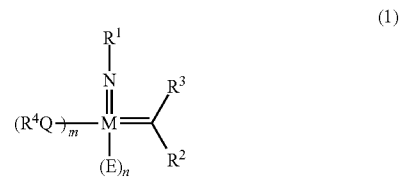

(In the above general formula (1), $R^1$ is selected from alkyl, aryl, and substituted aryl. $R^2$ and $R^3$ are independently selected from hydrogen, alkyl, aryl, substituted aryl, alkylsilyl, and alkenyl; and they may be the same with or different from each other. $R^4$ is selected from alkyl, halogenated alkyl, aryl, and substituted aryl. N is a nitrogen atom and Q is an oxygen or a sulfur atom. E is a molecule having a coordinating property and selected from ether, alkylphosphine, arylphosphine, alkoxyphosphine, pyridine, alkylamine, and alkylidene amine. M is a transition metal atom selected from the group 3 to the group 12 of the periodic table. m is an integer from equal to or more than 1 to equal to or less than 3, and when m is 2 or 3, $R^4$ may be combined with each other. n is an integer from equal to or more than 0 to equal to or less than 2.)

[5] the metathesis catalyst according to [4], wherein, in the metathesis catalyst represented by the above general formula (1), the transition metal atom M selected from the group 3 to the group 12 of the periodic table, is one selected from the group consisting of tantalum, vanadium, molybdenum, tungsten, rhenium, ruthenium, and osmium, and m is 1 or 2 and n is 0 or 1;

[6] the metathesis catalyst according to [4] or [5], wherein the content of an alkali metal is equal to or less than 10 ppm;

[7] a metathesis catalyst represented by the following general formula (1) and the content of an alkali metal is equal to or less than 10 ppm;

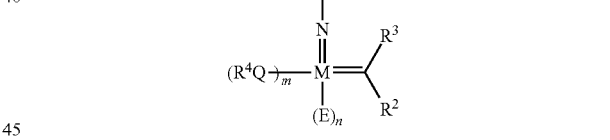

(In the above general formula (1), $R^1$ is selected from alkyl, aryl, and substituted aryl. $R^2$ and $R^3$ are independently selected from hydrogen, alkyl, aryl, substituted aryl, alkylsilyl, and alkenyl, and they may be the same with or different from each other. $R^4$ is selected from alkyl, halogenated alkyl, aryl, and substituted aryl. N is a nitrogen atom and Q is an oxygen or a sulfur atom. E is a molecule having a coordinating property and selected from ether, alkylphosphine, arylphosphine, alkoxyphosphine, pyridine, alkylamine, and alkylidene amine. M is a transition metal atom selected from the group 3 to the group 12 of the periodic table. m is an integer from equal to or more than 1 to equal to or less than 3, and when m is 2 or 3, $R^4$ may be combined with each other. n is an integer from equal to or more than 0 to equal to or less than 2.)

[8] a process for producing a metathesis catalyst wherein the process for producing an organic transition metal complex compound according to any one of [1] to [3] is used;

[9] a ring-opening metathesis polymer obtainable by polymerizing a cyclic olefin in the presence of the metathesis catalyst according to any one of [4] to [7]; and

[10] a process for producing a ring-opening metathesis polymer, wherein the process includes polymerizing a cyclic olefin in the presence of the metathesis catalyst according to any one of [4] to [7].

With the process for producing an organic transition metal complex compound of the present invention, the organic transition metal complex compound can be prepared in an industrially and economically efficient manner.

Since a metathesis catalyst obtainable by being synthesized with the use of the process for producing an organic transition metal complex compound of the present invention, is reduced in the content of an alkali metal, a ring-opening metathesis polymer polymerized with the use of the catalyst can be subjected to a hydrogenation reaction without removing the alkali metal beforehand.

Moreover, the ring-opening metathesis polymer and the hydrogenated polymer thereof can be preferably utilized for an application of, for example, electronic materials or the like which are strictly limited in the content of an alkali metal, therefore they are extremely valuable industrially.

BRIEF DESCRIPTION OF THE DRAWING

The above purpose and other purposes, features, and advantages will be clearer with reference to the following preferable embodiments and the accompanying drawing.

The drawing shows a $^1$H-NMR spectrum of the organic transition metal complex compound obtained in an Example.

BEST MODE FOR CARRYING OUT THE INVENTION

The process for producing an organic transition metal complex compound according to the present invention, a metathesis catalyst obtainable by being produced with the use of the process a ring-opening metathesis polymer obtainable by polymerizing a cyclic olefin with the use of the metathesis catalyst, and the process for producing the polymer, will be described in detail below.

The process for producing an organic transition metal complex compound according to the present invention, includes: in the presence of a basic compound;
with (A) an organic transition metal complex compound with an atom group having an electron-withdrawing ability;
contacting (B) a compound having a proton-donor ability, thus converting the atom group having an electron-withdrawing ability of (A) the organic transition metal complex compound with an atom group having an electron-withdrawing ability, into an atom group having an electron-withdrawing ability derived from (B) the compound having a proton-donor ability, and obtaining (C) an organic transition metal complex compound. The process for producing an organic transition metal complex compound can convert any atom group having an electron-withdrawing ability into an atom group having a stronger electron-donor ability, by contacting any compound having an proton-donor ability with an organic transition metal complex compound with any atom group having an electron-withdrawing ability in the presence of any basic compound.

Hereinafter, each component used in the present invention is explained by using specific examples, but the present invention is not limited to the following compounds. In the present invention, the exemplified compounds may be used independently or in combination of two or more of them.

Unless otherwise indicated in the present specification, Me represents a methyl group, $^i$Pr an iso-propyl group, $^t$Bu a tert-butyl group, Ph a phenyl group, and Ad an adamantyl group. PMe$_3$ represents a trimethylphosphine, and P(OMe)$_3$ a trimethoxyphosphine. "dme" represents 1, 2-dimethoxyethan, and "thf" represents a tetrahydrofuran.

In the present invention, a basic compound refers to a molecule or a proton acceptor having an unshared electron pair for coordination. Such basic compound is, for example, a basic organic compound. The basic compound preferably contains no alkali metal.

Specific examples of the organic basic compounds include: nitrogen-containing basic organic compounds such as; primary amines, such as ammonium and methylamine; secondary amines, such as diphenylamine; tertiary amines, such as triethylamine, ethyldiisopropylamine; and nitrogen-containing heterocyclic compounds such as 1, 4-diazabicyclo[2, 2, 2]octane, pyridine, and lutidine; and phosphorus-containing basic organic compounds such as phosphine.

Among these, triethylamine, ethyldiisopropylamine, pyridine, lutidine, and 1, 4-diazabicyclo[2, 2, 2]octane are particularly preferable. Two or more of them may be used in combination at any ratio.

An electron-withdrawing ability refers to a strong electronegativity. An atom group having an electron-withdrawing ability refers to an atom group having a strong electronegativity, and examples thereof include halogen, halogen-containing allyl or arylsulfonate, alkyl or arylsulfonate, halogen-containing phosphate, halogen-containing alkyl or arylcarboxylate, and alkyl or arylcarboxylate. Specific examples of atom groups having an electron-withdrawing ability include fluorine, chlorine, bromine, iodine, trifluoromethanesulfonate, that is, triflate, toluenesulfonate, hexafluorophosphate, and trifluoroacetate. Among them, chloride, trifluoromethanesulfonate, and toluenesulfonate are particularly preferable. Two or more of them may be used in combination.

(A) The organic transition metal complex compound with an atom group having an electron-withdrawing ability in the present invention, is a compound which has at least one or more atom group having an electron-withdrawing ability which can be substituted by an atom group having an electron-withdrawing ability derived from (B) a compound having a proton-donor ability which has a stronger electron-donor ability than the atom group having an electron-withdrawing ability of (A) the organic transition metal complex compound with an atom group having an electron-withdrawing ability. Moreover, (A) the organic transition metal complex compound with an atom group having an electron-withdrawing ability may have any ligand in addition to the atom group having an electron-withdrawing ability, and an example thereof includes a ligand containing a neutral, a cationic, or an anionic atom group having one or more atoms.

(A) The organic transition metal complex compound with an atom group having an electron-withdrawing ability is preferably an organic transition metal complex compound with a metal alkylidene or a metal alkylidyne, or a precursor thereof.

The organic transition metal complex compound with a metal alkylidene or a metal alkylidyne refers to an organic transition metal complex compound with a metal alkylidene or a metal carbene in which the organic transition metal complex compound with an atom group having an electron-withdrawing ability forms a double bond or a triple bond having a free valence of bivalence or trivalence between a transition metal central atom and a carbon at an α-position, or refers to an organic transition metal complex compound with a metal alkylidyne or a metal carbine in which a triple bond is formed between a transition metal and a carbon.

A precursor of the organic transition metal complex compound with a metal alkylidene or a metal alkylidyne refers to an organic metal complex compound capable of forming a metal alkylidene or a metal alkylidyne, by heating or contacting with an organometallic reagent after being subjected to a treatment such as alkylation as a catalyst, while the precursor itself does not form a double bond or a triple bond having a free valence of bivalence or trivalence between a transition metal central atom and a carbon at the α-position.

Examples of the organic transition metal complex compounds with a metal alkylidene or a metal alkylidyne include, for example: $W(=CH^tBu)(=N-2, 6-Me_2C_6H_3)(dme)Cl_2$, $W(=CH^tBu)(=N-2, 6-^iPr_2C_6H_3)Cl_2(dme)$, $W(=CHCH=CPh_2)(O)Cl_2(thf)$, $W(=CHCH=CPh_2)(=N-2, 6-^iPr_2C_6H_3)Cl_2(PMe_3)$, $W(=CHCH=CPh_2)(=N-2, 6-^iPr_2C_6H_3)Cl_2-[P(OMe)_3]$, $W(=CHCH=CMePh)(=N-2, 6-Me_2C_6H_3)Cl_2(PMe_3)_2$, $Mo(=CHCMe_2Ph)(=N-2, 6-^iPr_2C_6H_3)(OSO_2CF_3)_2(dme)$, $Mo(=CHCMe_2Ph)(=N-2, 6-Me_2C_6H_3)(OSO_2CF_3)_2(dme)$, $Mo(=CH^tBu)(=N-2, 6-Me_2C_6H_3)(OSO_2CF_3)_2(dme)$, $Mo(=CHCMe_3)(=N-2, 6-Cl_2C_6H_3)(OSO_2CF_3)_2(dme)$, $Mo(=CHSiMe_3)(=N-Ad)(OSO_2CF_3)_2(dme)$, $Ta(=CHCMe_3)Cl_2[OCMe(CH_2PPh_2)_2]$, $Mo(=CHSiMe_3)(=N-2, 6-Me_2C_6H_3)(OCMe_2CF_3)_2(PMe_3)$, $W(\equiv C^tBu)(O^tBu)_2(OSO_2CF_3)_2(dme)$, $W(\equiv C^tBu)(dme)Cl_3$, $W(NH-2, 6-^iPr_2C_6H_3)(\equiv C^tBu)(dme)Cl_2$, $Re(\equiv C^tBu)(=CHMe)(OCMe_2CF_3)_2(dme)$, $W(\equiv C^tBu)(O^tBu)_3$.

Examples of the precursors of the organic transition metal complex compounds with a metal alkylidene or a metal alkylidyne include: $W(=N-2, 6-Me_2C_6H_3)Cl_4$, $[Et_4N][W(\equiv C^tBu)Cl_4]$, $W(=N-2, 6-Me_2C_6H_3)(CH_2^tBu)_2Cl_2$ $(thf)_2$, $Mo(=N-2, 6-^iPr_2C_6H_3)Cl_4(thf)_2$, $Os(=N-2, 6-^iPr_2C_6H_3)(CH_2^tBu)_2Cl_2$, $Os(=N-2, 6-^iPr_2C_6H_3)Cl_4$, $V(=N-2, 6-Me_2C_6H_3)Cl_3$, $V(=N-2, 6-Me_2C_6H_3)(NR_2)Cl_2$.

In the present invention, (B) a compound having a proton-donor ability may be any compound as long as the compound is capable of donating a proton. The compound is capable of eliminating a proton by contacting with (A) the organic transition metal complex compound with an atom group having an electron-withdrawing ability in the presence of a basic compound, then substituting (A) the organic transition metal complex compound with an atom group having an electron-withdrawing ability, with an atom group having a stronger electron-donor ability derived from (B) the compound having a proton-donor ability. In other words, the electron-donor ability of the atom group having an electron-withdrawing ability derived from (B) the compound having a proton-donor ability, is stronger than the electron-donor ability of the atom group having an electron-withdrawing ability of (A) the organic transition metal compound with an atom group having an electron-withdrawing ability.

In the present invention, (B) the compound having a proton-donor ability may or may not be the same compound as the basic compound.

Specific examples of (B) compounds having a proton-donor ability include: alcohols such as tert-butyl alcohol(2-methyl-2-propanol), 1, 1, 1, 3, 3, 3-hexafluoro-2-methyl-2-propanol, perfluoro-tert-butyl alcohol, phenol, 2, 6-diisopropylphenol, 2, 6-dichlorophenol, 2, 2'-biphenol, 3, 3'-di-tert-butyl-5, 5', 6, 6'-tetramethyl-2, 2'-dihydroxybiphenyl;
carboxylic acid;
sulfonic acid;
amines such as primary amine, and secondary amine such as dimethylamine; and
thiols such as 2-methyl-2-propanethiol, benzothiol, and 4-tert-butylthiophenol. Among them, (B) the compound having a proton-donor ability is preferably at least one or more selected from the alcohols and the thiols. The alcohol may include an alcoholic hydroxyl group or a phenolic hydroxyl group.

(B) The compound having a proton-donor ability may be at least one or more selected from the alcohols and the thiols, and (A) the organic transition metal complex compound with an atom group having an electron-withdrawing ability may be an organic transition metal complex compound with a metal alkylidene or a metal alkylidyne.

(B) The compound having a proton-donor ability may have a single proton or be multifunctional having two or more protons, and these compounds may contain a halogen, a silicon, a cyano, an ether, or an ester as well. These compounds may be used independently or in combination of two or more of them.

(C) The organic transition metal complex compound in the present invention is an organic transition metal complex compound having a transition metal atom from the group 3 to the group 12 of the periodic table (long period form) as a central metal, and preferably having a transition metal atom from the group 4 to the group 9. Examples of such transition metal atoms include, for example: titanium, vanadium, niobium, tantalum, molybdenum, tungsten, rhenium, ruthenium, osmium and rhodium, preferably tantalum, vanadium, molybdenum, tungsten, rhenium, ruthenium, and osmium, more preferably molybdenum, or tungsten.

Examples of (C) the organic transition metal complex compounds include, for example: alkylidene complex compound, alkylidyne complex compound, Fisher carbene complex compound, metallocene complex compound, and post-metallocene complex compound.

When (A) the organic transition metal complex compound with an atom group having an electron-withdrawing ability is, in particular, an organic transition metal complex compound with a metal alkylidene or a metal alkylidyne, (C) the organic transition metal complex compound can be preferably used as a catalyst or a precursor of a catalyst for the metathesis polymerization, the ring-opening metathesis reaction, the ring-closing metathesis reaction, or the cross-metathesis reaction or the like.

In the present invention, the amount of each component used when contacting (B) the compound having a proton-donor ability with (A) the organic transition metal complex compound with an atom group having an electron-withdrawing ability in the presence of a basic compound, will be determined as follows:

At first, the used amount of (B) the compound having a proton-donor ability to 1 mol of (A) the organic transition metal complex compound with an atom group having an electron-withdrawing ability, is, for example, equal to or more than 0.1 mol, preferably equal to or more than 0.2 mol. In addition, the used amount of (B) the compound having a proton-donor ability to 1 mol of (A) the organic transition metal complex compound with an atom group having an electron-withdrawing ability, is, for example, equal to or less than 100 mol, preferably equal to or less than 10 mol.

The used amount of the basic compound to 1 mol of (B) the compound having a proton-donor ability, is, for example, equal to or more than 0.1 mol, preferably equal to or more than 0.2 mol. In addition, the used amount of the basic compound to the 1 mol of (B) the compound having a proton-donor ability, is, for example, equal to or less than 100 mol, preferably equal to or less than 10 mol. However, the above amount of the basic compound is not limited thereto when the basic compound also serves as a solvent.

The contact form between (A) the organic transition metal complex compound with an atom group having an electron-withdrawing ability, and (B) the compound having a proton-donor ability is not particularly limited, and may be any one of the following forms: contact without a solvent, suspension contact in an organic solvent, uniform solution contact in these media, and contact in a gaseous phase.

When using an organic solvent, specific examples thereof include: a hydrocarbon such as pentane, hexane, toluene, and xylene;
an ether such as diethylether, tetrahydrofuran, dioxane, and dimethoxyethane;
a halogenated hydrocarbon such as dichloromethane, dichloroethane, chloroform, and chlorobenzene; and
basic compounds such as pyridine and piperidine. They may be used independently or in combination of two or more of them.

The compounds are contacted with each other at a temperature of, for example, equal to or higher than −100° C., preferably equal to or higher than −80° C. In addition, the compounds are contacted with each other at a temperature of, for example, equal to or lower than 200° C., preferably equal to or lower than 100° C.

The compounds may be contacted with each other under nitrogen or an inert gas atmosphere such as argon, and may be contacted with each other at a pressure of, for example, equal to or more than the ambient pressure. In addition, the pressure is, for example, equal to or less than 10 MPa, preferably equal to or less than 1.0 MPa.

The compounds may be contacted with each other, for example, equal to or more than 0.1 hour, preferably equal to or more than 0.5 hours, more preferably equal to or more than 1 hour. In addition, the contact period is, for example, equal to or less than one month, preferably equal to or less than 200 hours, more preferably equal to or less than 50 hours.

(C) The organic transition metal complex compound obtainable by the process of the present invention may be purified after being isolated or separated as needed. The purification may be carried out appropriately in combination of known processes, such as general distillation, extraction, liquid separation, concentration, deposition, recrystallization, filtration, washing, or drying. Such operations are carried out at a temperature of from about −100° C. to about 300° C., and under a pressure of from about $1 \times 10^{-6}$ MPa to about 10 MPa, which can be selected appropriately in accordance with each process.

The process of the present invention can be preferably used for preparing, for example, a metathesis catalyst represented by the following general formula (1). In the present invention, (C) the organic transition metal complex compound may be a metathesis catalyst.

[Chem. 3]

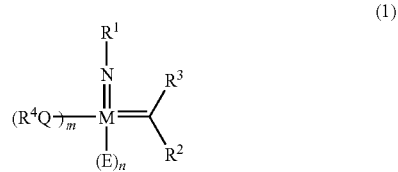

(1)

In the above general formula (1), $R^1$ is selected from alkyl, aryl, and substituted aryl, and particularly, alkyl, aryl, and substituted aryl having the number of carbon atoms of from equal to or more than 4 to equal to or less than 30, more preferably having the number of carbon atoms of from equal to or more than 4 to equal to or less than 20. Specifically, tert-butyl, phenyl, 4-tert-buthylphenyl, 2, 6-dimethylphenyl, 2, 6-diisopropylmethyl, 1-naphtyl, 2, 6-dichlorophenyl, 4-fluoro-2, 6-dimethylphenyl, and adamantyl or the like are preferably exemplified.

In the above general formula (1), $R^2$ and $R^3$ are selected from hydrogen, alkyl, aryl, substituted aryl, alkylsilyl, and alkenyl. $R^2$ and $R^3$ may be the same with or be different from each other, and particularly preferably, hydrogen, and alkyl, aryl, substituted aryl, alkylsilyl, and alkenyl having the number of carbon atoms of from equal to or more than 4 to equal to or less than 20. Specifically, hydrogen, methyl, ethyl, isopropyl, tert-butyl, 2-phenyl-2-propyl, phenyl, 1-naphtyl, trimethylsilyl, 2, 2-dimethylvinyl, 2-methyl-2-phenylvinyl, 2, 2-diphenylvinyl or the like are preferably exemplified.

In the above general formula (1), $R^4$ is selected from alkyl, halogenated alkyl, aryl, substituted aryl, and particularly preferably alkyl, halogenated alkyl, aryl, and substituted aryl having the number of carbon atoms of from equal to or more than 4 to equal to or less than 20. Specifically, isopropyl, perfluoropropyl, tert-butyl, perfluoro-n-butyl, 1, 1, 1-trifluoro-2-methyl-2-propyl, 1, 1, 1, 3, 3, 3-hexafluoro-2-methyl-2-propyl, perfluoro-tert-butyl, phenyl, 1-naphtyl, 2, 6-diisopropylphenyl, 2, 6-dimethylphenyl, 2, 6-dichlorophenyl, 2, 2'-biphenyl or the like are preferably exemplified.

In the above general formula (1), N is a nitrogen atom and Q is an oxygen or a sulfur atom.

E is a molecule having a coordinating property selected from ether, alkylphosphine, arylphosphine, alkoxyphosphine, pyridine, alkylamine, and alkylidene amine. Specifically, as for E, dimethylether, tetrahydrofuran, trimethylphosphine, triphenylphosphine, trimethoxyphosphine, pyridine, lutidine, triethylamine, propylideneamine or the like are preferably exemplified.

In the above general formula (1), M is a transition metal atom selected from the group 3 to the group 12 of the periodic table (long period form), and preferably, a transition metal atom selected from the group 4 to the group 9. Examples of such transition metal atoms include, for example, titanium, vanadium, niobium, tantalum, molybdenum, tungsten, ruthenium, osmium and rhodium, preferably, tantalum, vanadium, molybdenum, tungsten, rhenium, ruthenium, and osmium, more preferably, molybdenum, or tungsten. In addition, M may be one selected from the group consisting of tantalum, vanadium, molybdenum, tungsten, rhenium, ruthenium, and osmium, and m may be 1 or 2 and n be 0 or 1.

In the above general formula (1), m is an integer of from equal to or more than 1 to equal to or less than 3, preferably 1 or 2. When m is 2 or 3, $R^4$ may be bound with each other, and specifically, 3, 3'-di-tert-butyl-5, 5', 6, 6'-tetramethyl-2, 2'-biphenyl or the like is exemplified. In addition, n is an integer of from equal to or more than 0 to equal to or less than 2, preferably 0 or 1.

The metathesis catalyst in the above general formula (1) is not limited as long as the catalyst can carry out the metathesis reaction and the polymerization; however, examples thereof include, for example:

tungsten-based alkylidene catalysts, such as W(=N-2, 6-$R^5R^6C_6H_3$)(=CHR$^7$)(OR$^8$)$_2$ including W(=N-2, 6-$^iPr_2C_6H_3$)(=CH$^t$Bu)(O$^t$Bu)$_2$, W(=N-2, 6-$^iPr_2C_6H_3$)(=CH$^t$Bu)(OCMe$_2$CF$_3$)$_2$, W(=N-2, 6-$^iPr_2C_6H_3$)(=CH$^t$Bu)[OCMe(CF$_3$)$_2$]$_2$, and W(=N-2, 6-$^iPr_2C_6H_3$)(=CH$^t$Bu)[OC(CF$_3$)$_3$]$_2$; W(=N-2, 6-$R^5R^6C_6H_3$)(=CHR$^7$)(SR$^9$)$_2$ including W(=N-2, 6-$^iPr_2C_6H_3$)(=CH$^t$Bu)(S$^t$Bu)$_2$; W(=N-2, 6-$R^5R^6C_6H_3$)(=CHR$^7$)(OR$^8$)$_2$Py including W(=N—R$^{10}$)(=CHR$^7$)(OR$^8$)$_2$, W(=N—R$^{10}$)(=CHR$^7$)(SR$^9$)$_2$, W(=N-2, 6-$R^5R^6C_6H_3$)(=CHR$^7$)(OR$^8$)$_2$P(R$^{11}$)$_3$, W(=N-2, 6-$R^5R^6C_6H_3$)(=CHR$^7$)(SR$^9$)$_2$P(R$^{11}$)$_3$, W(=N—

$R^{10})(=CHR^7)(OR^8)_2P(R^{11})_3$, $W(=N-R^{10})(=CHR^7)(SR^9)_2P(R^{11})_3$, and $W(=CHCMe_2Ph)(=N-2, 6-^iPr_2C_6H_3)(O-2, 6-Cl_2C_6H_3)_2(Py)$; $W(=N-2, 6-R^5R^6C_6H_3)(=CHR^7)(SR^9)_2Py$; $W(=N-R^{10})(=CHR^7)(OR^8)_2Py$; and $W(=N-R^{10})(=CHR^7)(SR^9)_2Py$;

(wherein, $R^5$ and $R^6$ are H, alkyl groups such as $^iPr$, Me, and $^tBu$, alkoxy groups such as OMe, or halogens; $R^7$ is an alkyl group, an aryl group, or a silicon residue such as $^tBu$, $CMe_2Ph$, $CH=CMe_2$, $CH=CMePh$, $CH=CPh_2$, Ph, and $SiMe_3$; $R^8$ is an alkyl group, a halogenated alkyl group, or an aryl group such as $^tBu$, $CMe_2CF_3$, $CMe(CF_3)_2$, $C(CF_3)_3$, $C_6H_5$, 2-$^tBuC_6H_4$, 2-$^tBu$-4, 5-$Me_2C_6H$, and 2, 6-$Cl_2C_6H_3$; $R^9$ is an alkyl group, a halogenated alkyl group, or an aryl group such as $^tBu$, $CMe_2CF_3$, $CMe(CF_3)_2$, $C(CF_3)_3$, Ph, 2-$^tBuC_6H_4$, 2-$^tBu$-4, 5-$Me_2C_6H$; $R^{10}$ is an alkyl group such as $^tBu$ and adamantyl; $R^{11}$ is H, an alkyl group such as Me, an alkoxy group such as OMe, or an aryl group such as Ph; Py is a pyridine derivative such as pyridine and lutidine, or an amine derivative such as trimethylamine and propyldeneamine; Me is a methyl group; $^iPr$ is an iso-propyl group; $^tBu$ is a tert-butyl group; OMe is a methoxy group; Ph is a phenyl group)

molybdenum-based alkylidene catalysts, such as $Mo(=N-2, 6-R^5R^6C_6H_3)(=CHR^7)(OR^8)_2$ including $Mo(=N-2, 6-^iPr_2C_6H_3)(=CH^tBu)(O^tBu)_2$, $Mo(=N-2, 6-^iPr_2C_6H_3)(=CH^tBu)(OCMe_2CF_3)_2$, $Mo(=N-2, 6-^iPr_2C_6H_3)(=CH^tBu)[OCMe(CF_3)_2]_2$, $Mo(=N-2, 6-^iPr_2C_6H_3)(=CH^tBu)[OC(CF_3)_3]_2$, $Mo(=N-2, 6-Me_2C_6H_3)(=CH^tBu)[OC(CF_3)_3]_2$, $Mo(=CHCMe_2Ph)(=N-2, 6-Me_2C_6H_3)[OC(CF_3)_3]_2$, $Mo(=N-2, 6-^iPr_2C_6H_3)(=CH^tBu)(S^tBu)_2$, and $Mo(=CHCMe_2Ph)(=N-2, 6-^iPr_2C_6H_3)[OC(CF_3)_3]_2$; $Mo(=N-2, 6-R^5R^6C_6H_3)(=CHR^7)(SR^9)_2$ including $Mo(=CHCMe_2Ph)(=N-2, 6-^iPr_2C_6H_3)(S^tBu)_2$; $Mo(=N-R^{10})(=CHR^7)(OR^8)_2$ including $Mo(=CHSiMe_3)(=N-Ad)(O-2, 6-^iPr_2C_6H_3)_2$; $Mo(=N-R^{10})(=CHR^7)(SR^9)_2$; $Mo(=N-2, 6-R^5R^6C_6H_3)(=CHR^7)(OR^8)_2P(R^{11})_3$; $Mo(=N-2, 6-R^5R^6C_6H_3)(=CHR^7)(SR^9)_2P(R^{11})_3$; $Mo(=N-R^{10})(=CHR^7)(OR^8)_2P(R^{11})_3$; $Mo(=N-R^{10})(=CHR^7)(SR^9)_2P(R^{11})_3$; $Mo(=N-2, 6-R^5R^6C_6H_3)(=CHR^7)(OR^8)_2Py$; $Mo(=N-2, 6-R^5R^6C_6H_3)(=CHR^7)(SR^9)_2Py$; $Mo(=N-R^{10})(=CHR^7)(OR^8)_2Py$; and $Mo(=N-R^{10})(=CHR^7)(SR^9)_2PY$ (wherein $R^5$ and $R^6$ are H, alkyl groups such as $^iPr$, Me, and $^tBu$, alkoxy groups such as OMe, or halogens; $R^7$ is an alkyl group, an aryl group, or a silicon residue such as $^tBu$, $CMe_2Ph$, $CH=CMe_2$, $CH=CMePh$, $CH=CPh_2$, Ph, and $SiMe_3$; $R^8$ is a alkyl group, a halogenated alkyl group, or an aryl group such as $^tBu$, $CMe_2CF_3$, $CMe(CF_3)_2$, $C(CF_3)_3$, $C_6H_5$, 2-$^tBuC_6H_4$, 2-$^tBu$-4, 5-$Me_2C_6H_2$, and two of $R^8$ may be bound with each other. $R^9$ is an alkyl group, a halogenated alkyl group, or an aryl group such as $^tBu$, $CMe_2CF_3$, $CMe(CF_3)_2$, $C(CF_3)_3$, Ph, 2-$^tBuC_6H_4$, 2-$^tBu$-4, 5-$Me_2C_6H_2$, and two of $R^9$ may be bound with each other. $R^{10}$ is an alkyl group such as $^tBu$ and adamantyl, $R^{11}$ is H, an alkyl group such as Me, an alkoxy group such as OMe, or an aryl group such as Ph, Py is a pyridine derivative such as pyridine, and lutidine, or an amine derivative such as trimethylamine and propyrideneamine, Me is an methyl group, $^iPr$ is an iso-propyl group, $^tBu$ is a tert-butyl group, OMe is a methoxy group, and Ph is a phenyl group);

vanadium-based alkylidene catalysts, such as $V(=N-2, 6-R^5R^6C_6H_3)(=CHR^7)(OR^8)$, $V(=N-2, 6-R^5R^6C_6H_3)(=CHR^7)(SR^9)$, $V(=N-R^1)(=CHR^7)(OR^8)_2$, $V(=N-R^{10})(=CHR^7)(SR^9)$, $V(=N-2, 6-R^5R^6C_6H_3)(=CHR^7)(OR^8)P(R^{11})_3$, $V(=N-2, 6-R^5R^6C_6H_3)(=CHR^7)(SR_9)P(R^1)$, $V(=N-R^{10})(=CHR^7)(OR^8)P(R^{11})_3$, $V(=N-R^{10})(=CHR^7)(SR^9)P(R^{11})_3$, $V(=N-2, 6-R^5R^6C_6H_3)(=CHR^7)(OR^8)Py$, $V(=N-2, 6-R^5R^6C_6H_3)(=CHR^7)(SR^9)_2Py$, $V(=N-R^{10})(=CHR^7)(OR^8)Py$, $V(=N-R^{10})(=CHR^7)(SR^9)_2Py$;

(wherein $R^5$ and $R^6$ are H, alkyl groups such as $^iPr$, Me, $^tBu$, alkoxy groups such as OMe, or halogens, $R^7$ is an alkyl group, an aryl group, or a silicon residue such as $^tBu$, $CMe_2Ph$, $CH=CMe_2$, $CH=CMePh$, $CH=CPh_2$, Ph, and $SiMe_3$, $R^8$ is an alkyl group, a halogenated alkyl group, or an aryl group such as $^tBu$, $CMe_2CF_3$, $CMe(CF_3)_2$, $C(CF_3)_3$, $C_6H_5$, 2-$^tBuC_6H_4$, 2-$^tBu$-4, 5-$Me_2C_6H$, $R^9$ is an alkyl group, a halogenated alkyl group, or an aryl group such as $^tBu$, $CMe_2CF_3$, $CMe(CF_3)_2$, $C(CF_3)_3$, Ph, 2-$^tBuC_6H_4$, 2-$^tBu$-4, 5-$Me_2C_6H$, $R^{10}$ is an alkyl group such as $^tBu$ and adamantyl, $R^{11}$ is H, an alkyl group such as Me, an alkoxy group such as OMe, or an aryl group such as Ph, Py is a pyridine derivate such as pyridine and lutidine, or an amine derivative such as triethylamine and propylideneamine, Me is a methyl group, $^iPr$ is an iso-propyl group, $^tBu$ is a tert-butyl group, OMe is a metoxy group, and Ph is a phenyl group)

osmium-based alkylidene catalysts, such as $Os(=N-2, 6-R^5R^6C_6H_3)(=CHR^7)(OR^8)_2$ including $Os(=N-2, 6-Me_2C_6H_3)(CH_2^tBu)_2(O^tBu)_2$; $Os(=N-2, 6-R^5R^6C_6H_3)(=CHR^7)(SR^9)_2$, $Os(=N-R^{10})(=CHR^7)(OR^8)_2$, $Os(=N-R^{10})(=CHR^7)(SR^9)_2$, $Os(=N-2, 6-R^5R^6C_6H_3)(=CHR^7)(OR^8)_2P(R^{11})_3$, $Os(=N-2, 6-R^5R^6C_6H_3)(=CHR^7)(SR^9)_2P(R^{11})_3$, $Os(=N-R^{10})(=CHR^7)(OR^8)_2P(R^{11})_3$, $Os(=N-R^{10})(=CHR^7)(SR^9)_2P(R^{11})_3$, $Os(=N-2, 6-R^5R^6C_6H_3)(=CHR^7)(OR^8)_2Py$, $Os(=N-2, 6-R^5R^6C_6H_3)(=CHR^7)(SR^9)_2Py$, $Os(=N-R^6)(=CHR^7)(OR^8)_2Py$, $Os(=N-R^{10})(=CHR^7)(SR^9)_2Py$ (wherein $R^5$ and $R^6$ are H, alkyl groups such as $^iPr$, Me, and $^tBu$, alkoxy groups such as OMe, or halogens, $R^7$ is an alkyl group, an aryl group, or a silicon residue such as $^tBu$, $CMe_2Ph$, $CH=CMe_2$, $CH=CMePh$, $CH=CPh_2$, Ph and $SiMe_3$, $R^8$ is an alkyl group, a halogenated alkyl group, or an aryl group such as $^tBu$, $CMe_2CF_3$, $CMe(CF_3)_2$, $C(CF_3)_3$, $C_6H_5$, 2-$^tBuC_6H_4$, 2-$^tBu$-4, 5-$Me_2C_6H$, $R^9$ is an alkyl group, a halogenated alkyl group, or an aryl group such as $^tBu$, $CMe_2CF_3$, $CMe(CF_3)_2$, $C(CF_3)_3$, Ph, 2-$^tBuC_6H_4$, 2-$^tBu$-4, 5-$Me_2C_6H$, $R^{10}$ is an alkyl group such as $^tBu$, adamantyl, $R^{11}$ is H, an alkyl group such as Me, an alkoxy group such as OMe, or an aryl group such as Ph, Py is a pyridine derivative such as pyridine, and lutidine, or an amine derivative such as triethylamine, propylideneamine, Me is a methyl group, $^iPr$ is an iso-propyl group, $^tBu$ is a tert-butyl group, OMe is a methoxy group, and Ph is a phenyl group); and ruthenium-based alkylidene catalyst such as $Ru(=CHCH=CPh_2)(PPh_3)_2Cl_2$ (wherein Ph is a phenyl group).

As (C) the organic transition metal complex compound, a metathesis catalyst made from a combination of an organic transition metal complex as a precursor of a metathesis catalyst, and a Lewis acid as a co-catalyst, can also be cited. For example, the organic transition metal complex compounds described below and co-catalysts including organic aluminum compounds, such as trimethylalminum, diethylalminumchloride, and methylalminoxane, or organic tin compounds such as tetramethyltin, can be cited. Examples of the above organic transition metal complex compounds include: $W(=N-2, 6-Me_2C_6H_3)(thf)(O^tBu)_2X_2$ including $W(=N-2, 6-Me_2C_6H_3)(O^tBu)_2Cl_2$; $Mo(=N-2, 6-^iPr_2C_6H_3)(thf)(O^tBu)_2X_2$; $V(=N-2, 6-Me_2C_6H_3)(O^tBu)X_2$ including $V(=N-2, 6-Me_2C_6H_3)[OC(CF_3)_3]Cl_2$; $Os(=N-2, 6-^iPr_2C_6H_3)(O^tBu)_2X_2$, $W(=N-2, 6-Me_2C_6H_3)(thf)(O^tBu)_2R_2$, $Mo(=N-2, 6-^iPr_2C_6H_3)(thf)(O^tBu)_2R_2$, $V(=N-2, 6-Me_2C_6H_3)(PR_3)(O^tBu)R_2$, and $Os(=N-2, 6-^iPr_2C_6H_3)(O^tBu)_2R_2$, wherein $^iPr$ represents an iso-propyl group, $^tBu$ represents a tert-butyl group, R represents an alkyl group, X represents a halogen, and thf represents a tetrahydrofuran. These ring-opening metathesis catalysts may be used independently or in combination of two or more of them.

In the process for producing (C) the organic transition metal complex compound of the present invention, an atom group having an electron-withdrawing ability of (A) the organic transition metal complex compound with an atom group having an electron-withdrawing ability, can be converted into an atom group having a stronger electron-donor ability, by using a basic compound and (B) the compound having a proton-donor ability. In this process, since the compound having a proton-donor ability is not required to be an alkali metal salt, (C) the organic transition metal complex compound can be obtained without the use of a compound containing an alkali metal. Therefore, the concentration of an alkali metal in (C) the organic transition metal complex compound can be reduced.

For example, in the metathesis catalyst represented by the above general formula (1), the content of an alkali metal may be, for example, equal to or less than 10 ppm, preferably equal to or less than 5 ppm, more preferably equal to or less than 2 ppm.

The content of an alkali metal in the metathesis catalyst is, for example, equal to or more than 0 ppm. A less content of an alkali metal in the catalyst is preferable in view that the occurrence of a side reaction caused by the alkali metal is more surely prevented; however, the alkali metal may be contained in an amount not to impair the purpose of the present invention, and the amount may be, for example, about 0.001 ppm.

In a metathesis catalyst obtained with the use of a conventional process, since an alkali metal in the metathesis catalyst is contained as an alkali metal salt, a side reaction with a reaction substrate occurs during the metathesis polymerization reaction, when the content of the alkali metal is high, as described above, resulting in possibly affecting the properties of the polymer thus-produced adversely. When carrying out a hydrogenation reaction of a polymer produced with the use of a metathesis catalyst having too high content of an alkali metal, the alkali metal salt remaining in the polymer reacts with a hydrogenation catalyst to deteriorate or decompose itself, resulting in possible hindrance to a normal hydrogenation reaction.

With the concentration of an alkali metal in a metathesis catalyst being in the above range, the quality deterioration of a product can be more surely prevented during the metathesis polymerization reaction and the subsequent hydrogenation.

In the present invention, an alkali metal refers to lithium, sodium, and potassium, and the content of an alkali metal means the total amount of the above alkali metals in a metathesis catalyst.

Since the metathesis catalyst represented by the above general formula (1) can be obtained without the use of a compound containing an alkali metal, it is possible that an alkali metal is not substantially contained in the metathesis catalyst except for an alkali metal inevitably contained in the metathesis catalyst. Specifically, the concentration of an alkali metal in the metathesis catalyst can be less than the detection limit in the inductively-coupled-plasma mass spectrometry (ICP-MS), more specifically, less than 10 ppb. Due to this, the quality deterioration of a product can be more surely prevented during the metathesis polymerization reaction and the subsequent hydrogenation.

Next, a metathesis polymer with the use of the metathesis catalyst represented by the above general formula (1) and a process for producing the same will be explained.

In the present invention, the ring-opening metathesis polymer can be obtained by polymerizing a cyclic olefin in the presence of the metathesis catalyst represented by the above general formula (1).

The process for producing the ring-opening metathesis polymer according to the present invention includes polymerizing a cyclic olefin in the presence of the metathesis catalyst represented by the above general formula (1).

For example, in the present invention, a ring-opening metathesis polymer can be obtained by polymerizing the cyclic olefin represented by the following general formula (2) or the following general formula (3), with the use of the metathesis catalyst represented by the above general formula (1). In addition, a metathesis catalyst made from a combination of the above organic transition metal complex as a precursor of a metathesis catalyst, and a Lewis acid as a co-catalyst, can also be used.

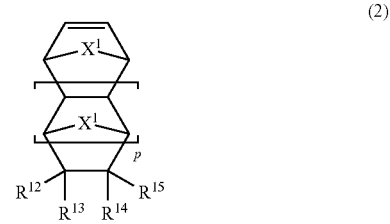

(2)

(In the above general formula (2), $R^{12}$ to $R^{15}$ are independently selected from the group consisting of hydrogen, alkyl group having the number of carbon atoms of from equal to or more than 1 to equal to or less than 20, aryl group having the number of carbon atoms of from equal to or more than 6 to equal to or less than 20, halogen, halogenated alkyl group having the number of carbon atoms of from equal to or more than 1 to equal to or less than 20, alkoxy group having the number of carbon atoms of from equal to or more than 1 to equal to or less than 20, alkoxyalkyl group having the number of carbon atoms of from equal to or more than 2 to equal to or less than 20, alkoxycarbonyl group having the number of carbon atoms of from equal to or more than 2 to equal to or less than 20, aryloxycarbonyl group having the number of carbon atoms of from equal to or more than 6 to equal to or less than 20, hydroxy group, hydroxyalkyl group having the number of carbon atoms of from equal to or more than 1 to equal to or less than 20, acid anhydride, cyano group, and silicon-containing group. $R^{12}$ to $R^{15}$ may be bound with each other to form a cyclic structure. $X^1$ is selected from —O—, —S—, —NR$^{16}$—, —PR$^{16}$—, and —CR$^{16}_2$—, and may be the same with or different from each other. ($R^{16}$ represents hydrogen, alkyl group having the number of carbon atoms of from equal to or more than 1 to equal to or less than 20.) p represents 0 or an integer of from equal to or more than 1 to equal to or less than 3.)

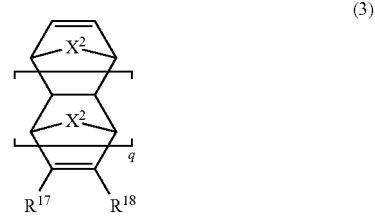

(3)

(In the above general formula (3), $R^{17}$ and $R^{18}$ are independently selected from the group consisting of hydrogen, alkyl group having the number of carbon atoms of from equal to or more than 1 to equal to or less than 20, aryl group having the number of carbon atoms of from equal to or more than 6 to equal to or less than 20, halogen, halogenated alkyl group having the number of carbon atoms of from equal to or more than 1 to equal to or less than 20, alkoxy group having the number of carbon atoms of from equal to or more than 1 to equal to or less than 20, alkoxyalkyl group having the number of carbon atoms of from equal to or more than 2 to equal to or less than 20, alkoxycarbonyl group having the number of carbon atoms of from equal to or more than 2 to equal to or less than 20, aryloxycarbonyl group having the number of carbon atoms of from equal to or more than 6 to equal to or less than 20, hydroxy group, hydroxyalkyl group having the number of carbon atoms of from equal to or more than 1 to equal to or less than 20, acid anhydride, cyano group, and silicon-containing group. $R^{17}$ and $R^{18}$ may be bound with each other to form a cyclic structure. $X^2$ is selected from —O—, —S—, —NR$^{19}$—, —PR$^{19}$—, and —CR$^{19}_2$—, and may be the same with or different from each other. ($R^{19}$ represents hydrogen and alkyl group having the number of carbon atoms of from equal to or more than 1 to equal to or less than 20.) q is 0, or an integer of from equal to or more than 1 to equal to or less than 3.)

In the present invention, as a cyclic olefin polymerized with the use of a metathesis catalyst, which is represented by the above general formula (2) or the above general formula (3), a derivative of bicycloheptene obtained when p or q is 0, a derivative of tetracyclododecene obtained when p or q is 1, a derivative of hexacycloheptadecene obtained when p or q is 2, and a derivative of octacyclodococene obtained when p or q is 3, or the like, can be cited.

Hereinafter, the above general formulae (2) and (3) will be explained in more detail.

At first, the general formula (2) will be explained.

Specific examples of $R^{12}$ to $R^{15}$ in the above general formula (2) include the following.

Examples of $R^{12}$ to $R^{15}$ include, for example, hydrogen.

Examples of alkyl groups having the number of carbon atoms of from equal to or more than 1 to equal to or less than 20, include methyl, ethyl, propyl, isopropyl, n-butyl, tert-butyl, cyclohexyl, and menthyl.

Examples of aryl groups having the number of carbon atoms of from equal to or more than 6 to equal to or less than 20, include alkyl substituted aryls such as phenyl, naphthyl, and methyl.

Examples of halogens include chlorine atom, bromine atom, iodine atom, and fluorine atom.

Examples of halogenated alkyl groups having the number of carbon atoms of from equal to or more than 1 to equal to or less than 20, include fluoromethyl, chloromethyl, bromomethyl, difluoromethyl, dichloromethyl, dibromomethyl, trifluoromethyl, trichloromethyl, and tribromomethyl.

Examples of alkoxy groups having the number of carbon atoms of from equal to or more than 1 to equal to or less than 20, include methoxy, ethoxy, isopropoxy, n-butoxy, tert-butoxy, and menthoxy.

Examples of alkoxyalkyl groups having the number of carbon atoms of from equal to or more than 2 to equal to or less than 20, include methoxymethyl, methoxyethyl, tert-butoxymethyl, tert-butoxyethyl, methoxymenthol, and alkoxy saccharides such as methylglucose.

Examples of alkoxycarbonyl groups having the number of carbon atoms of from equal to or more than 2 to equal to or less than 20, include methoxycarbonyl, ethoxycarbonyl, n-propoxycarbonyl, isopropoxycarbonyl, n-butoxycarbonyl, tert-butoxycarbonyl, 1-methylcyclopentyloxycarbonyl, 1-ethylcyclopentyloxycarbonyl, 1-ethylnorbonyloxycarbonyl, 1-ethyladamantyloxycarbonyl, cyclohexyloxycarbonyl, tetrahydropiran-2-yloxycarbonyl, tetrahydrofuran-2-yloxycarbonyl, 1-ethoxyethoxycarbonyl, and 1-butoxyethoxycarbonyl.

Examples of aryloxycarbonyl groups having the number of carbon atoms of from equal to or more than 6 to equal to or less than 20, include phenoxycarbonyl.

Hydroxy groups also are cited.

Examples of hydroxyalkyl groups having the number of carbon atoms of from equal to or more than 1 to equal to or less than 20, include hydroxymethyl, hydroxyethyl, hydroxypropyl, hydroxybutyl, hydroxyhexyl, menthol, and hydroxyalkyl groups including succharides such as glucose.

Examples of acid anhydrides include carboxylic anhydride.

Examples of cyano groups include cyano groups having the number of carbon atoms of from equal to or more than 1 to equal to or less than 20, such as nitrile, cyanomethyl or cyanoethyl.

Examples of silicon-containing groups include trialkylsilyl groups having the number of carbon atoms of from equal to or more than 3 to equal to or less than 20, such as trimethylsilyl, triethylsilyl, tripropylsilyl, triisopropylsilyl, tributylsilyl, triisobutylsilyl, tri-tert-butylsilyl, tripentylsilyl, and trihexylsilyl; trialkylsilyloxy groups having the number of carbon atoms of from equal to or more than 3 to equal to or less than 20 such as trimethylsilyloxy, triethylsilyloxy, tripropylsilyloxy, triisopropylsilyloxy, tributylsilyloxy, triisobutylsilyloxy, tri-tert-butylsilyloxy, tripentylsilyloxy, and trihexylsilyloxy;
trialkylsilyloxycarbonyl groups having the number of carbon atoms of from equal to or more than 3 to equal to or less than 20 such as trimethylsilyloxycarbonyl, triethylsilyloxycarbonyl, tripropylsilyloxycarbonyl, tributylsilyloxycarbonyl, triisobutylsilyloxycarbonyl, tri-tert-butylsilyloxycarbonyl, tripentylsilyloxycarbonyl, and trihexylsilyloxycarbonyl.

In the above general formula (2), $R^{12}$ to $R^{15}$ may be bound with each other to form a cyclic structure. Examples of such cyclic structures include, for example, cyclic alkyl structure capable of forming a cyclohexyl ring, cyclic ester structure capable of forming a lactone ring, cyclic imide structure capable of forming a phenylmaleimide ring, and acid anhydride structure capable of forming a carboxylic anhydride.

In the above general formula (2), $X^1$ is selected from —O—, —S—, —NR$^{16}$—, —PR$^{16}$—, and —CR$^{16}_2$. $R^{16}$ represents hydrogen or an alkyl group having the number of carbon atoms of from equal to or more than 1 to equal to or less than 20. p is 0 or an integer of from equal to or more than 1 to equal to or less than 3, and preferably 0 or 1. When p is an integer of from equal to or more than 1 to equal to or less than 3, $X^1$ may be the same with or different from each other. Specific examples of $R^{16}$ of —NR$^{16}$—, —PR$^{16}$—, and —CR$^{16}_2$— include hydrogen, or alkyl groups having the number of carbon atoms of from equal to or more than 1 to equal to or less than 20, such as methyl, ethyl, n-propyl, isopropyl, n-butyl, tert-butyl, cyclohexyl, and menthyl.

Specific examples of the above general formula (2) in the present invention include cyclic olefins consisting of:
bicycloheptenes of which basic backbone is bicyclo [2.2.1] hept-2-ene;
tetracyclododecenes of which basic backbone is tetracyclo [4.4.0.1$^{2,5}$.1$^{7,10}$]-3-dodecene;
hexacycloheptadecenes of which basic backbone is hexacyclo [4.4.0.1$^{2,5}$.1$^{7,10}$]-4-heptadecene; and octacyclodococenes of which basic backbone is octacyclo [8.8.0.1$^{2,9}$.1$^{4,7}$.1$^{11,18}$.1$^{13,16}$.0$^{3,8}$.0$^{12,17}$]-5-dococene.

Examples of substituent groups of R$^{12}$ to R$^{15}$ described in the above general formula (2) include cyclic olefins having a substituent group selected from the group consisting of: alkyl groups having the number of carbon atoms of from equal to or more than 1 to equal to or less than 20; aryl groups having the number of carbon atoms of from equal to or more than 6 to equal to or less than 20; halogens; halogenated alkyl groups having the number of carbon atoms of from equal to or more than 1 to equal to or less than 20; alkoxy groups having the number of carbon atoms of from equal to or more than 1 to equal to or less than 20; alkoxyalkyl groups having the number of carbon atoms of from equal to or more than 2 to equal to or less than 20; alkoxycarbonyl groups having the number of carbon atoms of from equal to or more than 2 to equal to or less than 20; aryloxycarbonyl groups having the number of carbon atoms of from equal to or more than 6 to equal to or less than 20; hydroxy groups; hydroxyalkyl groups having the number of carbon atoms of from equal to or more than 1 to equal to or less than 20; acid anhydrides; or cyano groups. X$^1$ is selected from —O—, —S—, —NR$^{16}$—, —PR$^{16}$—, and —CR$^{16}{}_2$—. (R$^{16}$ represents hydrogen or an alkyl group having the number of carbon atoms of from equal to or more than 1 to equal to or less than 20.) Among them, the following compounds can also be exemplified as substituent groups of R$^{12}$ to R$^{15}$: 7-methylbicycloheptenes obtained by replacing the methylene (—CH$_2$—) of the bicycloheptenes by a methylmethylene (—CH(methyl)-); 7-oxabicycloheptenes obtained by replacing the methylene (—CH$_2$—) by a 7-oxa; 7-thiabicycloheptenes obtained by replacing the methylene (—CH$_2$—) by a thia (—S—); 7-azabicycloheptenes and 7-methyl-7-azabicycloheptenes obtained by replacing the methylene (—CH$_2$—) by an aza (—NH—) and a methylaza (—N(methyl)-); and 7-phosphorbicycloheptenes and 7-methyl-7-phosphorbicycloheptenes obtained by replacing the methylene (—CH$_2$—) by a phosphor (—PH—) and a methylphosphor (—P(methyl)-).

R$^{12}$ to R$^{15}$ may be bound with each other to form a cyclic structure. For example, examples of cyclic alkyl structures capable of forming a cyclohexyl ring include 1, 4, 4a, 5, 6, 7, 8, 8a-octahydro-1, 4-methano-naphthalene. Example of cyclic ester structures capable of forming a lactone ring include, for example, 4-oxa-tricyclo [5.2.1.0$^{2,6}$]-8-decene-3-one, or 4, 10-dioxa-tricyclo [5.2.1.0$^{2,6}$]-8-decene-3-one. Examples of cyclic imide structures of a phenylmaleimide ring include, for example, 4-cyclohexyl-4-aza-tricyclo [5.2.1.0$^{2,6}$]-8-decene-3,5-dione, and 4-cyclohexyl-4-aza-10-oxa-tricyclo[5.2.1.0$^{2.6}$]-8-decene-3, 5-dione. Examples of acid anhydrides capable of forming a carboxylic anhydride include, for example, 4-oxa-tricyclo [5.2.1.0$^{2,6}$]-8-decene-3, 5-dione, or 4,10-dioxa-tricyclo [5.2.1.0$^{2,6}$]-8-decene-3,5-dione, and 4-oxa-10-thia-tricyclo [5.2.1.0$^{2,6}$]-8-decene-3,5-dione.

Compounds obtained by replacing a certain group of the tetracyclododecenes, the hexacycloheptadecenes, and the octacyclodococenes, can also be exemplified in the same way as the bicycloheptenes. Examples of such compounds include, for example: methyltetracyclododecenes, methylhexacycloheptadecenes, or methyloctacyclodococenes obtained by replacing the methylene of X$^1$ by a methylmethylene (—CH(methyl)-); oxatetracyclododecenes, oxahexacycloheptadecenes, and oxaoctacyclodococenes obtained by replacing the methylene of X$^1$ by an oxa (—O—); thiatetracyclododecenes, thiahexacycloheptadecenes, or thiaoctacyclodococenes obtained by replacing the methylene of X$^1$ by a thia (—S—); azatetracyclododecenes or methylazatetracyclododecenes, azahexacycloheptadecenes or methylazahexacycloheptadecenes, azahexacycloheptadecenes or methylazahexacycloheptadecenes obtained by replacing the methylene of X$^1$ by an aza (—NH—) or a methylaza (—N (methyl)-); and phosphortetracyclododecenes, and methylphosphortetracyclododecenes obtained by replacing the methylene of X$^1$ by a phosphor (—PH—) or a methylphosphor (—P(methyl)-). X$^1$ may be the same with or different from each other.

The above general formula (3) will be subsequently explained in more detail.

Specific examples of R$^{17}$ and R$^{18}$ of the general formula (3) include, for example: hydrogen;

as alkyl groups having the number of carbon atoms of from equal to or more than 1 to equal to or less than 20, methyl, ethyl, propyl, isopropyl, n-butyl, tert-butyl, cyclohexyl, and menthyl;

as aryl groups having the number of carbon atoms of from equal to or more than 6 to equal to or less than 20, phenyl, naphthyl, or alkyl substituted aryls such as methyl;

as halogens, a chlorine atom, a bromine atom, a iodine atom, and a fluorine atom;

as halogenated alkyl groups having the number of carbon atoms of from equal to or more than 1 to equal to or less than 20, fluoromethyl, chloromethyl, bromomethyl, difluoromethyl, dichloromethyl, dibromomethyl, trifluoromethyl, trichloromethyl, and tribromomethyl;

as alkoxy groups having the number of carbon atoms of from equal to or more than 1 to equal to or less than 20, methoxy, ethoxy, isopropoxy, n-butoxy, tert-butoxy, and mentoxy;

as alkoxyalkyl groups having the number of carbon atoms of from equal to or more than 2 to equal to or less than 20, methoxymethyl, methoxyethyl, tert-butoxymethyl, tert-butoxyethyl, methoxymenthol, and alkoxy saccharides such as methylglucose; as alkoxycarbonyl groups having the number of carbon atoms of from equal to or more than 2 to equal to or less than 20, methoxycarbonyl, ethoxycarbonyl, n-propoxycarbonyl, isopropoxycarbonyl, n-butoxycarbonyl, tert-butoxycarbonyl, 1-methylcyclopentyloxycarbonyl, 1-ethylcyclopentyloxycarbonyl, 1-ethylnorbonyloxycarbonyl, 1-ethyladamantyloxycarbonyl, cyclohexyloxycarbonyl, tetrahydropiran-2-yloxycarbonyl, tetrahydrofuran-2-yloxycarbonyl, 1-ethoxyethoxycarbonyl, 1-butoxyethoxycarbonyl;

as aryloxycarbonyl groups having the number of carbon atoms of from equal to or more than 6 to equal to or less than 20, phenoxycarbonyl;

a hydroxy group;

as hydroxyalkyl groups having the number of carbon atoms of from equal to or more than 1 to equal to or less than 20, hydroxymethyl, hydroxyethyl, hydroxypropyl, hydroxybutyl, hydroxyhexyl or menthol, and hydroxyalkyl group containing saccharides such as glucose;

as an acid anhydride, carboxylic anhydride;

as cyano groups, cyano groups having the number of carbon atoms of from equal to or more than 1 to equal to or less than 20, such as nitrile, cyanomethyl or cyanoethyl; and as silicon-containing groups, trialkylsilyl groups having the number of carbon atoms of from equal to or more than 3 to equal to or less than 20, such as trimethylsilyl, triethylsilyl, tripropylsilyl, triisopropylsilyl, tributylsilyl, triisobutylsilyl, tri-tert-butylsilyl, tripentylsilyl, and trihexylsilyl;

trialkylsilyloxy groups having the number of carbon atoms of from equal to or more than 3 to equal to or less than 20, such as trimethylsilyloxy, triethylsilyloxy, tripropylsilyloxy, triisopropylsilyloxy, tributylsilyloxy, triisobutylsilyloxy, tri-tert-butylsilyloxy, tripentylsilyloxy, and trihexylsilyloxy; trialkylsilyloxycarbonyl groups having the number of carbon atoms of from equal to or more than 3 to equal to or less than 20, such as trimethylsilyloxycarbonyl, triethylsilyloxycarbonyl, tripropylsilyloxycarbonyl, tributylsilyloxycarbonyl, triisobutylsilyloxycarbonyl, tri-tert-butylsilyloxycarbonyl, tripentylsilyloxycarbonyl, and trihexylsilyloxycarbonyl.

$R^{17}$ and $R^{18}$ may be bound with each other to form a cyclic structure, and examples thereof include, for example, cyclic alkyl structure capable of forming a cyclohexyl ring, cyclic ester structure capable of forming a lactone ring, cyclic imide structure capable of forming a phenylmaleimide ring, and acid anhydride structure capable of forming an carboxylic anhydride.

In the above general formula (3), $X^2$ is selected from —O—, —S—, —$NR^{19}$—, —$PR^{19}$—, and —$CR^{19}_2$, wherein, $R^{19}$ represents hydrogen, or an alkyl group having the number of carbon atoms of from equal to or more than 1 to equal to or less than 20. q is 0 or an integer of from equal to or more than 1 to equal to or less than 3, preferably 0 or 1, and when q is an integer of from equal to or more than 1 to equal to or less than 3, $X^2$ may be the same with or different from each other. Examples of $R^{19}$ of —$NR^{19}$—, —$PR^{19}$—, or —$CR^{19}_2$— includes, for example, hydrogen or an alkyl group having the number of carbon atoms of from equal to or more than 1 to equal to or less than 20, such as methyl, ethyl, n-propyl, isopropyl, n-butyl, tert-butyl, cyclohexyl, or menthyl. $X^2$ is preferably —O—, —S—, or —$CH_2$—.

Specific examples of the above general formula (3) in the present invention include: cyclic olefins consisting of: bicycloheptadienes of which basic backbone is bicyclo [2.2.1] hepta-2, 5-diene;
tetracyclododecedienes of which basic backbone is tetracyclo [4.4.0.1$^{2,5}$.1$^{7,10}$]-3, 7-dodecadiene;
hexacycloheptadecadienes of which basic backbone is hexacyclo [4.4.0.1$^{2,5}$.1$^{7,10}$]-4, 11-heptadecadienes; and
octacyclodococadienes of which basic backbone is octacyclo [8.8.0.1$^{2,9}$.1$^{4,7}$.1$^{11,18}$.1$^{13,16}$.0$^{3,8}$.0$^{12,17}$]-5, 14-docosediene.

Examples of substituent groups of $R^{17}$ and $R^{18}$ described in the above general formula (3) include cyclic olefins having a substituent group selected from the group consisting of: hydrogen; alkyl groups having the number of carbon atoms of from equal to or more than 1 to equal to or less than 20; aryl groups having the number of carbon atoms of from equal to or more than 6 to equal to or less than 20; halogens; halogenated alkyl groups having the number of carbon atoms of from equal to or more than 1 to equal to or less than 20; alkoxy groups having the number of carbon atoms of from equal to or more than 1 to equal to or less than 20; alkoxyalkyl groups having the number of carbon atoms of from equal to or more than 2 to equal to or less than 20; alkoxycarbonyl groups having the number of carbon atoms of from equal to or more than 2 to equal to or less than 20; aryloxycarbonyl groups having the number of carbon atoms of from equal to or more than 6 to equal to or less than 20; hydroxy groups; hydroxyalkyl groups having the number of carbon atoms of from equal to or more than 1 to equal to or less than 20; acid anhydrides; or cyano groups. $X^2$ is selected from —O—, —S—, —$NR^{19}$—, —$PR^{19}$—, and —$CR^{19}_2$—. ($R^{19}$ represents hydrogen or an alkyl group having the number of carbon atoms of from equal to or more than 1 to equal to or less than 20.) Among them, the following compounds can also be exemplified as substituent groups of $R^{17}$ to $R^{18}$: 7-methylbicycloheptadienes obtained by replacing the methylene (—$CH_2$—) of the bicycloheptadienes by a methylmethylene (—CH (methyl)-); 7-oxabicycloheptadienes obtained by replacing the methylene (—$CH_2$—) by a 7-oxa; 7-thiabicycloheptadienes obtained by replacing the methylene (—$CH_2$—) by a thia (—S—); 7-azabicycloheptadienes and 7-methyl-7-azabicycloheptadienes obtained by replacing the methylene (—$CH_2$—) by a aza (—NH—) and a methylaza (—N(methyl)-); and 7-phosphorbicycloheptadienes and 7-methyl-7-phosphorbicycloheptadienes obtained by replacing the methylene (—$CH_2$—) by a phosphor (—PH—) or a methylphosphor (—P (methyl)-).

$R^{17}$ and $R^{18}$ may be bound with each other to form a cyclic structure. For example, examples of cyclic alkyl structures capable of forming a cyclohexyl ring include 1, 4, 5, 6, 7, 8-hexahydro-1,4-methano-naphthalene. Example of cyclic ester structures capable of forming a lactone ring include, for example, 4-oxa-tricyclo [5.2.1.0$^{2,6}$]-2,8-decadiene-3-one, or 4, 10-dioxa-tricyclo [5.2.1.0$^{2,6}$]-2, 8-decadiene-3-one. Examples of cyclic imide structures capable of forming a phenylmaleimide ring include, for example, 4-cyclohexyl-4-aza-tricyclo [5.2.1.0$^{2,6}$]-2, 8-decadiene-3, 5-dione, and 4-cyclohexyl-4-aza-10-oxa-tricyclo[5.2.1.0$^{2,6}$]-2, 8-decadiene-3, 5-dione. Examples of acid anhydride structures capable of forming a carboxylic anhydride include, for example, 4-oxa-tricyclo[5.2.1.0$^{2,6}$]-2, 8-decadiene-3, 5-dione, or 4, 10-dioxa-tricyclo[5.2.1.0$^{2,6}$]-2, 8-decadiene-3, 5-dione, and 4-oxa-10-thia-tricyclo[5.2.1.0$^{2,6}$]-2, 8-decadiene-3, 5-dione.

Compounds obtained by replacing a certain group of the tetracyclododecadienes, the hexacycloheptadecadienes, and the octacyclodococadienes, can also be exemplified in the same way as the bicycloheptadienes. Examples of such compounds include, for example: methyltetracyclododecadienes, methylhexacycloheptadecadienes or methyloctacyclodococadienes obtained by replacing the methylene of $X^2$ by a methylmethylene (—CH(methyl)-); oxatetracyclododecadienes, oxahexacycloheptadecadienes, or oxaoctacyclodococadienes obtained by replacing the methylene of $X^2$ by an oxa (—O—); thiatetracyclododecadienes, thiahexacycloheptadecadienes, or thiaoctacyclodococadienes obtained by replacing the methylene of $X^2$ by a thia (—S—); azatetracyclododecadienes, or methylazatetracyclododecadienes, azahexacycloheptadecadienes, or methylazahexacycloheptadecadienes, azahexacycloheptadecadienes, or methylazahexacycloheptadecadienes obtained by replacing the methylene of $X^2$ by an aza (—NH—) or a methylaza (—N(methyl)-); and phosphortetracyclododecadienes, and methylphosphortetracyclododecadienes obtained by replacing the methylene of $X^2$ by a phosphor (—PH—) or a methylphosphor (—P(methyl)-). $X^2$ may be the same with or different from each other.

Examples of other cyclic olefins used for polymerization include, for example: cycloolefins such as dicyclopentadiene, cyclopropene, cyclobutene, cyclopentene, cycloheptene, and cyclooctene;
cyclodienes such as cyclohexa-1, 4-diene, cyclohexa-1, 3-diene, cycloocta-1, 5-diene, cycloocta-1, 4-diene, and cycloocta-1, 3-diene; and
cyclotrienes such as cycloocta-1, 3, 5-trienes, and cycloocta-1, 3, 6-trienes.

The ring-opening metathesis polymer in the present invention may be one obtained by polymerizing at least one cyclic olefin selected from the group consisting of the above general formula (2), the above general formula (3), cycloolefins, cyclodienes, or cyclotrienes, or be one obtained by copolymerizing at least two cyclic olefins among them.

In polymerization with the use of the metathesis catalyst represented by the above general formula (1), as a monomer other than a cyclic olefin, acetylene, a derivative therefrom, and a derivative from diacetylene may be used independently, or be copolymerized with a cyclic olefin. In addition, a metathesis catalyst made from a combination of the above organic transition metal complex as a precursor of a metathesis catalyst, and a Lewis acid as a co-catalyst, can also be used.

In polymerization with the use of the metathesis catalyst represented by the general formula (1) of the present invention, the molar ratio of the cyclic olefin to 1 mol of the metathesis catalyst of tantalum, vanadium, molybdenum, tungsten, rhenium, ruthenium, and osmium, is, for example, equal to or more than 2, preferably equal to or more than 10. In addition, the molar ratio of the cyclic olefin to 1 mol of the above metathesis catalyst is, for example, equal to or less than 30,000, preferably equal to or less than 20,000.

In polymerization with the use of a metathesis catalyst made from a combination of the above organic transition metal complex as a precursor of a metathesis catalyst, and a Lewis acid as a co-catalyst, the molar ratio of the cyclic olefin to 1 mol of the organic transition metal complex is, for example, equal to or more than 2, preferably equal to or more than 10. In addition, the molar ratio of the cyclic olefin to 1 mol of the organic transition metal complex is, for example, equal to or less than 10,000, preferably equal to or less than 5,000.

The molar ratio of the organic metal compound as a co-catalyst to 1 mol of the organic transition metal complex is, for example, equal to or more than 0.01, preferably equal to or more than 0.1, more preferably equal to or more than 1. In addition, the molar ratio of the organic metal compound as a co-catalyst to 1 mol of the organic transition metal complex is, for example, equal to or less than 100, preferably equal to or less than 10, more preferably equal to or less than 5.

In the present invention, the polymerization of a cyclic olefin with the use of the metathesis catalyst may be carried out with or without a solvent. Examples of solvents used in the reaction include: ethers such as tetrahydrofuran, diethylether, dibutylether, dimethoxyethane, or dioxane; aromatic hydrocarbons such as benzene, toluene, xylene, and ethylbenzene;

aliphatic hydrocarbons such as pentane, hexane and heptane;
 aliphatic cyclic hydrocarbons such as cyclopentane, cyclohexane, methylcyclohexane, dimethylcyclohexane, or decalin; and
halogenated hydrocarbons such as methylenedichloride, dichloroethane, dichloroethylene, tetrachloroethane, chlorobenzene, or trichlorobenzene. Two or more of them may be used in combination.

In order to obtain a polymer having a desired molecular weight and a molecular weight distribution by enhancing the efficiency of a catalyst or by controlling the molar ratio of the cyclic olefin and the catalyst in the present invention, polymerization can be carried out in the presence of olefins or dienes as a chain transfer agent.

Examples of olefins used as a chain transfer agent include, for example: α-olefins such as ethylene, propylene, buten-1, pentene-1, hexene-1, and octene-1; silicon-containing olefins such as vinyltrimethylsilane, allyltrimethylsilane, allyltriethylsilane, and allyltriisopropylsilane; and as dienes, nonconjugated dienes such as 1, 4-pentadiene, 1, 5-hexadiene, and 1, 6-heptadiene. These olefins or dienes may be used independently or in combination of two or more of them, respectively.

With respect to the amount of use of an olefin or a diene present in the present invention, the molar ratio of the olefin or the diene to 1 mol of the cyclic olefin is equal to or more than 0.001, preferably equal to or more than 0.01. In addition, the molar ratio of the olefin or the diene to 1 mol of the cyclic olefin is equal to or less than 1000, preferably equal to or less than 100.

The equivalent ratio of the olefin or the diene to 1 equivalent amount of the metathesis catalyst is, for example, equal to or more than 0.01 equivalent amount, preferably equal to or more than 0.1 equivalent amount, more preferably equal to or more than 1 equivalent amount. In addition, the equivalent ratio of the olefin or the diene to 1 equivalent amount of the metathesis catalyst is, for example, equal to or less than 10,000 equivalent amount, preferably equal to or less than 1000 equivalent amount, more preferably equal to or less than 500 equivalent amount.

In polymerization of a cyclic olefin with the use of a metathesis catalyst, a concentration of the cyclic olefin in a polymerization solvent varies depending on the reactivity of the cyclic olefin and the solubility thereof in a polymerization solvent; however, the concentration of the cyclic olefin is preferably in the range of from about 0.1 to about 100 mol/L. Typically, a ring-opening metathesis polymer solution can be obtained by carrying out the polymerization reaction at a temperature of from about −30 to 150° C. for a period of from about 1 minute to about 10 hours, then stopping the reaction with the use of a quencher including aldehyde such as butylaldehyde, keton such as aceton, and alcohol such as methanol.

Specific examples of the ring-opening metathesis polymers obtained by polymerizing a cyclic olefin will be hereinafter described.

The repeat unit of the ring-opening metathesis polymer obtained by polymerizing the cyclic olefin represented by the above general formula (2) or the above general formula (3), can be represented by the following general formula (4) or the following general formula (5).

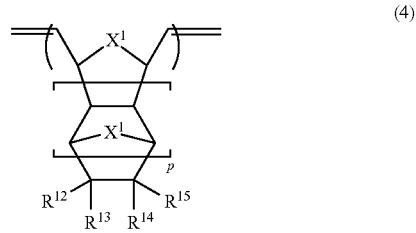

(4)

(In the above general formula (4), $R^{12}$ to $R^{15}$ are groups independently selected from the group consisting of: hydrogen; alkyl groups having the number of carbon atoms of from equal to or more than 1 to equal to or less than 20; aryl groups having the number of carbon atoms of from equal to or more than 6 to equal to or less than 20; halogens; halogenated alkyl groups having the number of carbon atoms of from equal to or more than 1 to equal to or less than 20; alkoxy groups having the number of carbon atoms of from equal to or more than 1 to equal to or less than 20; alkoxyalkyl groups having the number of carbon atoms of from equal to or more than 2 to equal to or less than 20; alkoxycarbonyl groups having the number of carbon atoms of from equal to or more than 2 to equal to or less than 20; aryloxycarbonyl groups having the number of carbon atoms of from equal to or more than 6 to equal to or less than 20; hydroxy groups; hydroxyalkyl groups having the number of carbon atoms of from equal to or more than 1 to equal to or less than 20; acid anhydrides; cyano groups; and silicon-containing groups. $R^{12}$ to $R^{15}$ may be bound with each other to form a cyclic structure. $X^1$ may be selected from —O—, —S—, —$NR^{16}$—, —$PR^{16}$—, and —$CR^{16}{}_2$, which may be the same with or different from each other. $R^{16}$ represents hydrogen and an alkyl group having the number of carbon atoms of from equal to or more than 1 to equal to or less than 20. p represents 0 or an integer of from equal to or more than 1 to equal to or less than 3.)

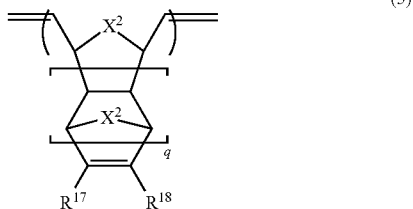

(In the general formula (5), $R^{17}$ and $R^{18}$ are independently selected from the group consisting of: hydrogen; alkyl groups having the number of carbon atoms of from equal to or more than 1 to equal to or less than 20; aryl groups having the number of carbon atoms of from equal to or more than 6 to equal to or less than 20; halogens; halogenated alkyl groups having the number of carbon atoms of from equal to or more than 1 to equal to or less than 20; alkoxy groups having the number of carbon atoms of from equal to or more than 1 to equal to or less than 20; alkoxyalkyl groups having the number of carbon atoms of from equal to or more than 2 to equal to or less than 20; alkoxycarbonyl groups having the number of carbon atoms of from equal to or more than 2 to equal to or less than 20; aryloxycarbonyl groups having the number of carbon atoms of from equal to or more than 6 to equal to or less than 20; hydroxy groups; hydroxyalkyl groups having the number of carbon atoms of from equal to or more than 1 to equal to or less than 20; acid anhydrides; cyano groups; and silicon-containing groups. $R^{17}$ and $R^{18}$ may be bound with each other to form a cyclic structure. $X^2$ is selected from —O—, —S—, —NR$^{19}$—, —PR$^{19}$—, and —CR$^{19}_2$, which may be the same with or different from each other. ($R^{19}$ represents hydrogen or an alkyl group having the number of carbon atoms of from equal to or more than 1 to equal to or less than 20.) q represents 0 or an integer of from equal to or more than 1 to equal to or less than 3.)

The weight average molecular weight (Mw) of the ring-opening metathesis polymer in the present invention, which is indicated as the weight average molecular weight of polystyrene which is determined by Gel Permeation Chromatography (GPC), is, for example, equal to or more than 2,000, preferably equal to or more than 5,000. In addition, the above Mw is, for example, equal to or less than 1,000,000, preferably equal to or less than 300,000.

The molecular weight distribution (Mw/Mn), which is a ratio of the weight average molecular weight (Mw) to the number average molecular weight (Mn), is preferably in a range of from equal to or more than 1.0 to equal to or less than 5.0.

Since the ring-opening metathesis polymer of the present invention contains no alkali metal salt in the metathesis catalyst, the polymerization solution can be directly hydrogenated to a double bond in the main chain of the ring-opening metathesis polymer, without a process of removing an alkali metal. In the process, hydrogen is added in an amount such that the hydrogenation ratio (a percentage of a ratio of the number of the hydrogenated double bonds to the number of the double bonds included in the polymer) is preferably in the range of from equal to or more than 50% to equal to or less than 100%, more preferably from equal to or more than 80% to equal to or less than 100%, in the presence of the hydrogenation catalyst.

The light transmittance of the hydrogenated polymer in the wavelength range of ultraviolet rays can be controlled by being saturated the double bonds in the main chain of the ring-opening metathesis polymer at an appropriate ratio by hydrogenation. The hydrogenated polymer exhibits enhanced antioxidative stability by hydrogenation. The ring-opening metathesis polymer can be made more easily available from the point of practical use, with the weather resistance and the heat resistance thereof being enhanced by reducing the number of the double bonds in the main chain, depending on applications.

The hydrogenated polymers of the ring-opening metathesis polymers represented by the above general formula (4) or the above general formula (5), are represented by the following general formula (6) or the following general formula (7).

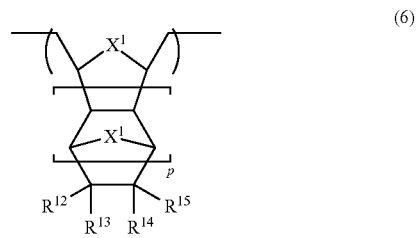

(In the above general formula (6), $R^{12}$ to $R^{15}$ are independently selected from the group consisting of: hydrogen; alkyl groups having the number of carbon atoms of from equal to or more than 1 to equal to or less than 20; aryl groups having the number of carbon atoms of from equal to or more than 6 to equal to or less than 20; halogens; halogenated alkyl groups having the number of carbon atoms of from equal to or more than 1 to equal to or less than 20; alkoxy groups having the number of carbon atoms of from equal to or more than 1 to equal to or less than 20; akoxyalkyl groups having the number of carbon atoms of from equal to or more than 2 to equal to or less than 20; alkoxycarbonyl groups having the number of carbon atoms of from equal to or more than 2 to equal to or less than 20; aryloxycarbonyl groups having the number of carbon atoms of from equal to or more than 6 to equal to or less than 20; hydroxy groups; hydroxyalkyl groups having the number of carbon atoms of from equal to or more than 1 to equal to or less than 20; acid anhydrides; cyano groups; and silicon-containing groups. $R^{12}$ to $R^{15}$ may be bound with each other to form a cyclic structure. $X^1$ is selected from —O—, —S—, —NR$^{16}$—, —PR$^{16}$—, and —CR$^{16}_2$—, which may be the same with or different from each other. ($R^{16}$ represents hydrogen or an alkyl group having the number of carbon atoms of from equal to or more than 1 to equal to or less than 20.) p is 0 or an integer of from equal to or more than 1 to equal to or less than 3.)

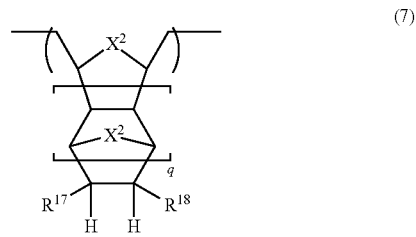

(In the above general formula (7), $R^{17}$ and $R^{18}$ are independently selected from the group consisting of: hydrogen; alkyl groups having the number of carbon atoms of from equal to or more than 1 to equal to or less than 20, aryl groups having the number of carbon atoms of from equal to or more than 6 to equal to or less than 20; halogens; halogenated alkyl groups having the number of carbon atoms of from equal to or more than 1 to equal to or less than 20; alkoxy groups having the number of carbon atoms of from equal to or more than 1 to equal to or less than 20; alkoxyalkyl groups having the number of carbon atoms of from equal to or more than 2 to equal to or less than 20; alkoxycarbonyl groups having the number of carbon atoms of from equal to or more than 2 to equal to or less than 20; aryloxycarbonyl groups having the number of carbon atoms of from equal to or more than 6 to equal to or less than 20; hydroxy groups; hydroxyalkyl groups having the number of carbon atoms of from equal to or more than 1 to equal to or less than 20; acid anhydrides; cyano groups; and silicon-containing groups. $R^{17}$ and $R^{18}$ may be bound with each other to form a cyclic structure. $X^2$ is selected from —O—, —S—, —NR$^{19}$—, —PR$^{19}$—, and —CR$^{19}{}_2$, which may be the same with or different from each other. ($R^{19}$ represents hydrogen or an alkyl group having the number of carbon atoms of from equal to or more than 1 to equal to or less than 20.) q represents 0 or an integer of from equal to or more than 1 to equal to or less than 3.)

The weight average molecular weight (Mw) of the hydrogenated ring-opening metathesis polymer in the present invention, which is indicated as the weight average molecular weight of polystyrene which is determined by Gel Permeation Chromatography (GPC), is preferably equal to or more than 2,000, more preferably equal to or more than 5,000. In addition, the above Mw is preferably equal to or less than 1,000,000, more preferably equal to or less than 300,000.

The molecular weight distribution (Mw/Mn), which is a ratio of the weight average molecular weight (Mw) to the number average molecular weight (Mn) of the hydrogenated ring-opening metathesis polymer, is preferably equal to or more than 1.0. In addition, (Mw/Mn) is preferably equal to or less than 5.0.

A known hydrogenation catalyst can be used for the hydrogenation reaction of the ring-opening metathesis polymer of the present invention.

Specific examples of hydrogenation catalysts for hydrogenating double bonds in the main chain of the ring-opening metathesis polymer, include: as for heterogeneous catalysts, supported-type metallic catalysts in which metals such as palladium, platinum, nickel, rhodium, and ruthenium are supported by carriers such as carbon, silicon, alumina, titania, magnesia, diatomaceous earth, and synthetic zeolite; and as for homogeneous catalysts, nickel naphthenate/triethylaluminum, nickel acetylacetonate/triisobutylaluminum, cobalt octenate/n-butyllithium, titanocenedichloride/diethylaluminum chloride, rhodium acetate, dichlorobis (triphenylphosphine) palladium, chlorotris (triphenylphosphine) rhodium, dihydridetetrakis (triphenylphosphine) ruthenium.

Specific examples of homogeneous catalysts include, dichlorobis (triphenyiphosphine) nickel, dichlorobis (triphenylphosphine) palladium, dichlorobis (triphenyiphosphine) platinum, chlorotris (triphenyiphosphine) rhodium, dichlorotris (triphenylphosphine) osmium, dichlorohydridebis (triphenylphosphine) iridium, dichlorotris (triphenylphosphine) ruthenium, dichlorotetrakis (triphenylphosphine) ruthenium, trichloronitrosylbis (triphenylphosphine) ruthenium, dichlorobis (acetonitrile) bis(triphenylphosphine) ruthenium, dichlorobis (tetrahydrofuran) bis(triphenylphosphine) ruthenium, chlorohydride (toluene) tris (triphenylphosphine) ruthenium, chlorohydridecarbonyltris (triphenylphosphine) ruthenium, chlorohydridecarbonyltris (diethylphenyl phosphine) ruthenium, ch lorohydridenitrosyltris (triphenylphosphine) ruthenium, dichlorotris (trimethylphosphine) ruthenium, dichlorotris (triethylphosphine) ruthenium, dichlorotris (tricyclohexylphosphine) ruthenium, dichlorotris (triphenylphosphine) ruthenium, dichlorotris (methyldiphenylphosphine) ruthenium, dichlorotris (dimethylphenylphosphine) ruthenium, dichlorotris (tri-o-tolylphosphine) ruthenium, dichlorotris (dichloroethylphosphine) ruthenium, dichlorotris (dichlorophenyl phosphine) ruthenium, dichlorotris (trimethylphosphate) ruthenium, and dichlorotris (triphenylphosphate) ruthenium.

These homogeneous catalysts may be used in combination with an amine compound.

Specific examples of amine compounds include: primary amine compounds such as methylamine, ethylamine, aniline, ethylenediamine, and 1, 3-diaminocyclobutane;

secondary amine compounds such as dimethylamine, methylisopropylamine and N-methylaniline;

tertiary amine compounds such as trimethylamine, triethylamine, triphenylamine, N,N-dimethylaniline, pyridine, and γ-picoline. Among them, the tertiary amine compounds are preferably used, in particular, when using the trimethylamine, the hydrogenation ratio is remarkably increased. These homogeneous catalysts or the amine compounds may be used in combination of two or more of them at any ratio, respectively.

When using the above known hydrogenation catalyst for hydrogenating the ring-opening metathesis polymer in the present invention, the amount of use of the known hydrogenation catalyst to the ring-opening metathesis polymer is, for example, equal to or more than 5 ppm, preferably equal to or more than 100 ppm. In addition, the amount of use of the known hydrogenation catalyst to the ring-opening metathesis polymer is, for example, equal to or less than 50,000 ppm, preferably equal to or less than 1,000 ppm.

When using a hydrogenation catalyst which is composed of a homogeneous catalyst and an amine compound, the amount of use of the homogeneous catalyst to the ring-opening metathesis polymer is, for example, equal to or more than 5 ppm, preferably equal to or more than 10 ppm, most preferably equal to or more than 50 ppm. In addition, the amount of use of the homogeneous catalyst to the ring-opening metathesis polymer is, for example, equal to or less than 50,000 ppm, preferably equal to or less than 10,000 ppm, most preferably equal to or less than 1,000 ppm.

The amount of use of the amine compound to 1 equivalent amount of the homogeneous catalyst is, for example, equal to or more than 0.1 equivalent amount, preferably equal to or more than 0.5 equivalent amount, most preferably equal to or more than 1 equivalent amount. In addition, the amount of use of the amine compound to 1 equivalent amount of the homogeneous catalyst is, for example, equal to or less than 1,000 equivalent amount, preferably equal to or less than 500 equivalent amount, most preferably equal to or less than 100 equivalent amount.

While a hydrogenation catalyst composed of a homogeneous catalyst and an amine compound can be used after the two components were contacted with each other, the two components may be respectively added directly to the reaction system, without contacting them beforehand.

A solvent used in the hydrogenation reaction of the ring-opening metathesis polymer may be any one as long as the solvent dissolves the ring-opening metathesis polymer and is not hydrogenated itself, and examples of such solvents include, for example: ethers such as tetrahydrofuran, diethylether, dibutylether, and dimethoxyethane;
aromatic hydrocarbons such as benzene, toluene, xylene, and ethylbenzene;
aliphatic hydrocarbons such as pentane, hexane, and heptane; aliphatic cyclic hydrocarbons such as cyclopentane, cyclohexane, methylcyclohexane, dimethylcyclohexane, and decalin; and
halogenated hydrocarbons such as methylenedichloride, dichloroethane, dichloroethylene, tetrachloroethane, chlorbenzene, and trichlorbenzene. Two or more of them may be used in combination.

In the hydrogenation reaction of the ring-opening metathesis polymer, the pressure of hydrogen is typically equal to or more than the ambient pressure, preferably equal to or more than 0.5 MPa, most preferably equal to or more than 2 MPa. In addition, the pressure of hydrogen is typically equal to or less than 30 MPa, preferably equal to or less than 20 MPa, most preferably equal to or less than 15 MPa. The reaction temperature of the hydrogenation reaction is typically equal to or higher than 0° C., preferably equal to or higher than room temperature, most preferably equal to or higher than 50° C. In addition, the reaction temperature is typically equal to or lower than 300° C., preferably equal to or lower than 250° C., most preferably equal to or lower than 200° C.

These conditions and a reaction period may be determined according to a desired rate of hydrogenation.

When the hydrogenation reaction of the ring-opening metathesis polymer being finished, the ring-opening metathesis catalyst or the hydrogenation catalyst remaining in the polymer can be removed with the use of a known process. Recovery of the hydrogenated polymer from the hydrogenated ring-opening metathesis polymer solution can be carried out with the use of a known process, without particularly being limited. For example, the following processes can be referred to: a process in which the reaction solution is discharged in a poor solvent under stirring so that the hydrogenated polymer is coagulated, then is recovered by the filtration process, the centrifugation process, the decantation process or the like; the steam stripping process in which steam is bubbled through the reaction solution to precipitate the hydrogenated polymer; and a process in which the solvent is directly removed from the reaction solution by heating or the like.

The metathesis catalyst of the present invention can be used as a reaction catalyst for organic synthetic reactions such as alkyne polymerization of acetylenes, and ring-closing metathesis reaction and cross metathesis reaction of organic compounds having a double bond or a triple bond. In the case, the metathesis reaction can also be practiced without a side reaction, as well as with the polymerization reaction. These metathesis reactions may be practiced in a suspension polymerization without a solvent, or be in a solution polymerization with the use of an organic solvent. Reaction conditions such as temperature, pressure, period, or concentration are not particularly limited.

According to the process for producing the organic transition metal complex compound of the present invention, the organic transition metal complex compound can be prepared in an industrially and economically efficient manner. The organic transition metal complex compound in the present invention can be used as, for example, alkylidene complex compound, alkylidyne complex compound, Fischer carbene complex compound, metallocene complex compound, and post-metallocene complex compound or the like, and also can be used as a catalyst for an organic synthesis reaction.

The metathesis catalyst obtainable by being synthesized with the use of the process for producing the organic transition metal complex compound of the present invention, can be reduced in its content of an alkali metal, and the content of an alkali metal may be, for example, equal to or less than 10 ppm. A ring-opening metathesis polymer such as a cyclic olefin polymerized with the use of the catalyst, can be subjected to a hydrogenation reaction without removing an alkali metal beforehand. Moreover, the ring-opening metathesis polymer or the hydrogenated polymer thereof can be preferably utilized for an application of, for example, electronic materials or the like which are strictly limited in the content of an alkali metal, therefore they are extremely valuable industrially.

EXAMPLES

The present invention will be further explained below with reference to examples, however, the invention is not limited to these examples.

In the following Examples and Comparative Examples, the obtained organic transition metal complex compound was dissolved in deuterated benzene and analyzed using $^1$H-NMR (270 MHz or 500 MHz).

The content of an alkali metal was measured by using Inductively Coupled Plasma Mass Spectrometry (ICP-MS). The detection limit of an alkali metal is 10 ppb.

The molecular weight of a polymer or a hydrogenated polymer was calibrated by a standard polystyrene conversion method using gel permeation chromatography (GPC) and 830-RI (manufactured by JASCO Corporation) as a detector and Shodexk-804, 803, and 802.5 as columns, after the ring-opening metathesis polymer obtained by polymerization and the hydrogenated polymer thereof are dissolved in a tetrahydrofuran.

The glass transition temperature (Tg) of the polymer was measured by using DSC-50 (manufactured by SHIMADZU CORPORATION) operating a heating rate at 10° C./minute under nitrogen.

Example 1

Mo(=CHCMe$_2$Ph)(=N-2, 6-$^i$Pr$_2$C$_6$H$_3$)(OSO$_2$CF$_3$)$_2$(dme)(1.00 g) was placed in a 50 mL round bottomed flask under nitrogen and suspended in diethylether then was added with triethylamine (0.27 g) at room temperature under stirring. Subsequently cooling to −30° C., perfluoro-tert-butyl alcohol (0.63 g) was added dropwise under stirring. Removing the solvent 3 hours later then extracting with pentane, the mixture was filtered and evaporated to dryness in vacuo to obtain 1.09 g of yellow solid. NMR spectrum of the solid indicated that Mo(=CHCMe$_2$Ph)(=N-2, 6-$^i$Pr$_2$C$_6$H$_3$)[OC(CF$_3$)$_3$]$_2$ was formed. No alkali metal was detected in the obtained solid.

Comparative Example 1

Comparative Example 1 was carried out according to Example 1 except that perfluoro-tert-butoxy lithium (0.64 g), which was synthesized under nitrogen from perfluoro-tert-butyl alcohol (5.0 g) and n-butyllithium (13.2 ml of 1.6M hexane solution) and purified, was used instead of triethylamine (0.27 g) and perfluoro-tert-butyl alcohol (0.63 g). The obtained solid was darkish and molybdenum complex, which was a starting material, and a decomposition product were mixed. Lithium was detected at 230 ppm in the obtained solid. Washing the obtained solid with 5 ml of pentane cooled to −30° C. two times, lithium was detected at 100 ppm or more.

Comparative Example 2

Comparative Example 2 was carried out according to Example 1 except that trimethylamine was not used. The obtained solid was a mixture of molybdenum complex, which was a starting material, and a decomposition product eliminating alkylidene. No alkali metal was detected in the obtained solid.

Example 2

Example 2 was carried out according to Example 1 except that 1, 1, 1, 3, 3, 3-hexafluoro-2-methyl-2-propanol (0.48 g) was used instead of perfluoro-tert-butyl alcohol in Example 1. 0.95 g of yellow solid were obtained. NMR spectrum of the solid indicated that Mo(=CHCMe$_2$Ph)(=N-2, 6-$^i$Pr$_2$C$_6$H$_3$)[OCMe(CF$_3$)$_2$]$_2$ was formed. No alkali metal was detected in the obtained solid.

Comparative Example 3

Comparative Example 3 was carried out according to Example 2 except that 1, 1, 1, 3, 3, 3-hexafluoro-2-methyl-propoxylithium (0.50 g), which was synthesized under nitrogen from 1, 1, 1, 3, 3, 3-hexafluoro-2-methyl-2-propanol (5.0 g) and n-butyllithium (18.9 ml of 1.6M hexane solutions) and purified, was used instead of triethylamine (0.27 g) and 1, 1, 1, 3, 3, 3-hexafluoro-2-methyl-2-propanol (0.48 g). 0.74 g of yellow solid were obtained.

NMR spectrum of the solid indicated that Mo(=CHCMe$_2$Ph) (=N-2, 6-$^i$Pr$_2$C$_6$H$_3$)[OCMe(CF$_3$)$_2$]$_2$ was formed. Lithium was detected at 200 ppm in the obtained solid.

Example 3

Mo(=CHCMe$_2$Ph)(=N-2, 6-$^i$Pr$_2$C$_6$H$_3$)(OSO$_2$CF$_3$)$_2$(dme)(1.00 g) was placed in a 50 ml round bottomed flask under nitrogen and suspended in about 10 ml of diethylether then was added with triethylamine (0.27 g) at room temperature under stirring. Subsequently cooling to −30° C. then 2-methyl-2-propanethiol (0.24 g) was added dropwise under stirring. Stirring for 3 hours at room temperature then removing the solvent followed by extracting with pentane, the mixture was filtered and evaporated to dryness in vacuo to obtain reddish brown solid. NMR spectrum of the solid indicated that Mo(=CHCMe$_2$Ph)(=N-2, 6-$^i$Pr$_2$C$_6$H$_3$)(S$^t$Bu)$_2$ was formed. The drawing shows $^1$H-NMR spectrum of the obtained solid. No alkali metal was detected in the obtained solid.

Comparative Example 4

Comparative Example 4 was carried out according to Example 3 except that 2-methyl-2-propothioxypotassium (0.34 g), which was synthesized under nitrogen from 2-methyl-2-propanethiol (5.0 g) and potassium hydride (2.2 g) and purified, was used instead of triethylamine (0.27 g) and 2-methyl-2-propanethiol (0.24 g). The obtained solid was a mixture of molybdenum complex, which was a starting material, and a decomposition product. Potassium was detected at 300 ppm in the obtained solid.

Example 4

Mo(=CH$^t$Bu)(=N-2, 6-Me$_2$C$_6$H$_3$)(OSO$_2$CF$_3$)$_2$(dme) (1.00 g) was placed in a 50 ml round bottomed flask under nitrogen and suspended in diethylether then was added with triethylamine (0.32 g) at room temperature under stirring. Subsequently cooling to −30° C., 2-methyl-2-propanol (0.23 g) was added dropwise under stirring. Removing the solvent 3 hours later then extracting with pentane, the mixture was filtered and evaporated to dryness in vacuo to obtain 0.65 g of yellow solid. NMR spectrum of the solid indicated that Mo(=CHCMe$_3$)(=N-2, 6-Me$_2$C$_6$H$_3$)(O$^t$Bu)$_2$ was formed. No alkali metal was detected in the obtained solid.

Example 5

Mo(=CHCMe$_2$Ph)(=N-2, 6-Me$_2$C$_6$H$_3$)(OSO$_2$CF$_3$)$_2$(dme)(1.00 g) was placed in a 50 ml round bottomed flask under nitrogen and suspended in diethylether then was added with triethylamine (0.30 g) at room temperature under stirring. Subsequently cooling to −30° C., perfluoro-tert-butyl alcohol (0.67 g) was added dropwise under stirring. Removing the solvent 16 hours later then extracting with pentane, the mixture was filtered and evaporated to dryness in vacuo to obtain 1.02 g of yellow solid. NMR spectrum of the solid indicated that Mo(=CHCMe$_2$Ph)(=N-2, 6-Me$_2$C$_6$H$_3$)[OC(CF$_3$)$_3$]$_2$ was formed. No alkali metal was detected in the obtained solid.

Example 6

Mo(=CHSiMe$_3$)(=N-Ad)(OSO$_2$CF$_3$)$_2$(dme)(1.00 g) was placed in a 50 ml round bottomed flask under nitrogen and suspended in diethylether then was added with triethylamine (0.29 g) at room temperature under stirring. Subsequently cooling to −30° C., 2, 6-diisopropylphenol (0.50 g) was added dropwise under stirring. Removing the solvent 3 hours later then extracting with pentane, the mixture was filtered and evaporated to dryness in vacuo to obtain 0.91 g of yellow solid. NMR spectrum of the solid indicated that Mo(=CHSiMe$_3$)(=N-Ad)(O-2, 6-$^i$Pr$_2$C$_6$H$_3$)$_2$ was formed. No alkali metal was detected in the obtained solid. Ad represents an adamantyl group.

Example 7

Mo(=CHCMe$_3$)(=N-2, 6-Cl$_2$C$_6$H$_3$)(OSO$_2$CF$_3$)$_2$(dme) (1.00 g) was placed in a 50 ml round bottomed flask under nitrogen and suspended in diethylether then was added with triethylamine (0.30 g) at room temperature under stirring. Subsequently cooling to −30° C., 3, 3'-di-tert-butyl-5, 5', 6, 6'-tetramethyl-2, 2'-dihydroxybiphenyl (0.51 g) was added dropwise under stirring. Removing the solvent 3 hours later then extracting with pentane, the mixture was filtered and evaporated to dryness in vacuo to obtain 1.00 g of yellow solid. NMR spectrum of the solid indicated that compound represented by the following formula (8) was formed. No alkali metal was detected in the obtained solid.

(8)

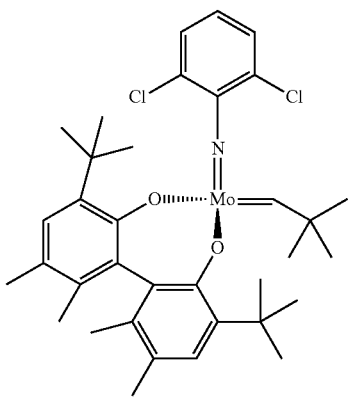

Example 8

W(=CHCH=CMePh)(=N-2, 6-Me$_2$C$_6$H$_3$)Cl$_2$(PMe$_3$)$_2$ (1.00 g) was placed in a 50 ml round bottomed flask under nitrogen and suspended in about 10 ml of diethylether then was added with triethylamine (0.37 g) at room temperature under stirring. Subsequently cooling to −30° C., 2-methyl-2-propanol (0.26 g) was added dropwise under stirring. Stirring for 3 hours at room temperature then removing the solvent followed by extracting with pentane, the mixture was filtered and evaporated to dryness in vacuo to obtain 0.90 g of yellow-brown solid. NMR spectrum of the solid indicated that W(=CHCH=CMePh)(=N-2,6-Me$_2$C$_6$H$_3$)(O$^t$Bu)$_2$PMe$_3$ was formed. No alkali metal was detected in the obtained solid.

Example 9

W(=CH$^t$Bu)(=N-2, 6-$^i$Pr$_2$C$_6$H$_3$)Cl$_2$(dme)(1.00 g) was placed in a 50 ml round bottomed flask under nitrogen and suspended in about 10 ml of diethylether then was added with triethylamine (0.36 g) at room temperature under stirring. Subsequently cooling to −30° C., 1, 1, 1, 3, 3, 3-hexafluoro-2-methyl-2-propanol (0.63 g) was added dropwise under stirring. Stirring for 3 hours at room temperature then removing the solvent followed by extracting with pentane, the mixture was filtered and evaporated to dryness in vacuo to obtain 0.88 g of yellow solid. NMR spectrum of the solid indicated that W(=CH$^t$Bu)(=N-2, 6-$^i$Pr$_2$C$_6$H$_3$)[OCMe(CF$_3$)$_2$]$_2$ was formed. No alkali metal was detected in the obtained solid.

Example 10

W(=N-2, 6-Me$_2$C$_6$H$_3$)Cl$_4$(thf) (1.00 g) was placed in a 50 ml round bottomed flask under nitrogen and suspended in about 10 ml of diethylether then was added with triethylamine (0.40 g) at room temperature under stirring. Subsequently cooling to −30° C., 2-methyl-2-propanol (0.30 g) was added dropwise under stirring. Stirring for 3 hours at room temperature then removing the solvent followed by extracting with pentane, the mixture was filtered and evaporated to dryness in vacuo to obtain 0.95 g of yellow solid. NMR spectrum of the solid indicated that W(=N-2, 6-Me$_2$C$_6$H$_3$)(O$^t$Bu)$_2$Cl$_2$ was formed. No alkali metal was detected in the obtained solid.

Example 11

[Et$_4$N][W(=C$^t$Bu)Cl$_4$] (1.00 g) was placed in a 50 ml round bottomed flask under nitrogen and suspended in about 10 ml of diethylether then was added with triethylamine (0.40 g) at room temperature under stirring. Subsequently cooling to −30° C., 2-methyl-2-propanol (0.29 g) was added dropwise under stirring. Stirring for 3 hours at room temperature then removing the solvent followed by extracting with pentane, the mixture was filtered and evaporated to dryness in vacuo to obtain yellowish white solid. NMR spectrum of the solid indicated that W(=C$^t$Bu)(O$^t$Bu)$_3$ was formed. No alkali metal was detected in the obtained solid.

Example 12

Tetracyclo [4.4.0.1$^{2.5}$.1$^{7.10}$]-3-dodecene (10.00 g) and 1, 5-hexadiene (50 mg) were dissolved in dry tetrahydrofuran (60 ml) under nitrogen and stirred at room temperature. The above solution was added with a solution in which Mo(=CHCMe$_2$Ph)(=N-2, 6-$^i$Pr$_2$C$_6$H$_3$)[OCMe(CF$_3$)$_2$]$_2$ (47 mg), which was synthesized in Example 2, was dissolved in dry tetrahydrofuran (2 ml), then was stirred at room temperature. The above solution was added 1 hour later with a solution in which n-butylaldehyde (18.5 mg, 0.25 mmol) was dissolved in dry tetrahydrofuran, thereby the reaction being stopped. When measuring the reaction ratio of 0.1 g of the reaction solution by using $^1$H-NMR, it was found that the polymerization reaction was driven to 100%. Another 1 g of the reaction solution was added into methanol to precipitate ring-opening metathesis polymer, which was filtered and separated followed by being dried in a vacuum to obtain white powder of the ring-opening metathesis polymer. The weight average molecular weight (Mw) of the ring-opening metathesis polymer measured by GPC was 20100, and the molecular weight distribution (Mw/Mn) was 1.52.

Comparative Example 5

Comparative Example 5 was carried out according to Example 12 except that Mo(=CHCMe$_2$Ph)(=N-2, 6-$^i$Pr$_2$C$_6$H$_3$)[OCMe(CF$_3$)$_2$]$_2$, which was synthesized in Comparative Example 3, was used instead of Mo(=CHCMe$_2$Ph) (=N-2, 6-$^i$Pr$_2$C$_6$H$_3$)[OCMe(CF$_3$)$_2$]$_2$ synthesized in Example 2. Taking 0.1 g of the reaction solution after the reaction was stopped, that the reaction ratio thereof was measured by using $^1$H-NMR, indicating that the polymerization reaction was driven to 98%. Another 1 g of the reaction solution was added into methanol to precipitate ring-opening metathesis polymer, which was filtered and separated followed by being dried in a vacuum to obtain white powder of the ring-opening metathesis polymer. The weight average molecular weight (Mw) of the ring-opening metathesis polymer measured by GPC was 23300, and the molecular weight distribution (Mw/Mn) was 1.70.

Example 13

50.0 g of the reaction solution synthesized in Example 12 was added with Ru(PPh$_3$)$_4$Cl$_2$ (5 mg) and triethylamine (1 mg) then subjected to a hydrogenation reaction at a hydrogen pressure of 10 MPa and at a temperature of 125° C. for 7 hours. After that, the temperature was reduced to room temperature and hydrogen gas was discharged. The hydrogenated ring-opening metathesis polymer solution was added into methanol to precipitate the hydrogenated ring-opening metathesis polymer, which was filtered and separated followed by being dried in a vacuum to obtain 7.7 g of white powder of the hydrogenated ring-opening metathesis polymer. The hydrogenation ratio of the hydrogenated ring-opening metathesis polymer thus-obtained, which was calculated from ¹H-NMR thereof, was 100% because no peak attributed to a proton of the olefin of the main chain was found. The weight average molecular weight (Mw) measured by GPC was 29200, and the molecular weight distribution (Mw/Mn) was 1.60.

Comparative Example 6

Comparative Example 6 was carried out according to Example 13 except that the reaction solution synthesized in Comparative Example 5 was used instead of the reaction solution synthesized in Example 12. The hydrogenated ring-opening metathesis polymer solution was added into methanol to precipitate the hydrogenated ring-opening metathesis polymer, which was filtered and separated followed by being dried in a vacuum to obtain 6.9 g of white powder of the hydrogenated ring-opening metathesis polymer. The hydrogenation ratio of the hydrogenated ring-opening metathesis polymer thus-obtained, which is calculated from ¹H-NMR thereof, was 80% because a peak attributed to a proton of the olefin of the main chain was found. The weight average molecular weight (Mw) measured by GPC was 32600, and the molecular weight distribution (Mw/Mn) was 2.01.

Example 14

Example 14 was carried out according to Example 1 except that pyridine (0.22 g) was used instead of triethylamine (0.27 g) in Example 1, and 1.07 g of yellow solid was obtained. NMR spectrum of the solid indicated that $Mo(=CHCMe_2Ph)(=N-2, 6\text{-}^iPr_2C_6H_3)[OC(CF_3)_3]_2$ was formed. No alkali metal was detected in the obtained solid.

Example 15

Example 15 was carried out according to Example 1 except that 2, 6-dimethylpyridine (0.29 g) was used instead of triethylamine (0.27 g) in Example 1, and 1.08 g of yellow solid was obtained. NMR spectrum of the solid indicated that $Mo(=CHCMe_2Ph)(=N-2, 6\text{-}^iPr_2C_6H_3)[OC(CF_3)_3]_2$ was formed. No alkali metal was detected in the obtained solid.

Example 16

$Os(=N-2, 6\text{-}^iPr_2C_6H_3)(CH_2{}^tBu)_2Cl_2$ (1.00 g) was placed in a 50 ml round bottomed flask under nitrogen and suspended in about 10 ml of diethylether then was added with triethylamine (0.37 g) at room temperature under stirring. Subsequently cooling to −30° C., 2-methyl-2-propanol (0.27 g) was added dropwise under stirring. Stirring for 3 hours at room temperature then removing the solvent followed by extracting with pentane, the mixture was filtered and evaporated to dryness in vacuo to obtain 0.84 g of yellow solid. NMR spectrum of the solid indicated that $Os(=N-2, 6\text{-}^iPr_2C_6H_3)(CH_2{}^tBu)_2(O^tBu)_2$ was formed. No alkali metal was detected in the obtained solid.

Example 17

$V(=N-2, 6\text{-}Me_2C_6H_3)Cl_3$ (1.00 g) was placed in a 50 ml round bottomed flask under nitrogen and suspended in about 10 ml of diethylether then was added with triethylamine (0.37 g) at room temperature under stirring. Subsequently cooling to −30° C., perfluoro-tert-butyl alcohol (0.86 g) was added dropwise under stirring. Stirring for 3 hours at room temperature then removing the solvent followed by extracting with pentane, the mixture was filtered and evaporated to dryness in vacuo to obtain 1.08 g of yellow solid. NMR spectrum of the solid indicated that $V(=N-2, 6\text{-}Me_2C_6H_3)[OC(CF_3)_3]Cl_2$ was formed. No alkali metal was detected in the obtained solid.

Example 18

8-tert-butyloxycarbonyl-tetracyclo[4.4.0.1$^{2,5}$.1$^{7,10}$]-3-dodecene (15 g) and 4-oxa-tricyclo[5.2.1.0$^{2,6}$]-8-decene-3,5-dione (8.8 g) were dissolved in 100 ml of dry tetrahydrofuran under nitrogen, and 300 mg of 1, 5-hexadiene was added thereto and stirred. The solution in which $Mo(=CHCMe_2Ph)(=N-2, 6\text{-}Me_2C_6H_3)[OC(CF_3)_3]_2$ (30 mg), which was synthesized in Example 5, was dissolved in dry tetrahydrofuran (2 ml), was added, then was stirred at room temperature. Subsequently, butylaldehyde (7 mg) was added and was stirred for 30 minutes. When measuring the reaction ratio of 0.1 g of the reaction solution by using ¹H-NMR, it was found that the polymerization reaction was driven to 100%. Another 1 g of the reaction solution was added into water to precipitate the ring-opening metathesis polymer, which was filtered and separated followed by being dried in a vacuum to obtain white powder of the ring-opening metathesis polymer. The weight average molecular weight (Mw) of the ring-opening metathesis polymer measured by GPC was 14500, the molecular weight distribution (Mw/Mn) was 1.68, and Tg was 155° C.

Example 19

50.0 g of the reaction solution synthesized in Example 18 was added with $Ru(H)(CO)(PPh_3)_3Cl$ (4 mg) and triethylamine (1 mg) then subjected to a hydrogenation reaction at a hydrogen pressure of 10 MPa and at a temperature of 125° C. for 7 hours. After that, the temperature was reduced to room temperature and hydrogen gas was discharged. The hydrogenated ring-opening metathesis polymer solution was added into methanol to precipitate the hydrogenated ring-opening metathesis polymer, which was filtered and separated followed by being dried in a vacuum to obtain 12.0 g of powder of the hydrogenated ring-opening metathesis polymer. The hydrogenation ratio of the hydrogenated ring-opening metathesis polymer thus-obtained, which is calculated from ¹H-NMR thereof, was 100% because no peak attributed to a proton of the olefin of the main chain was found. The weight average molecular weight (Mw) measured by GPC was 20200, the molecular weight distribution (Mw/Mn) was 1.75, and Tg was 125° C.

Example 20

The solution in which $Mo(=CHCMe_2Ph)(=N-2, 6\text{-}^iPr_2C_6H_3)[OCMe(CF_3)_2]_2$ (20 mg), which was synthesized in Example 2, was dissolved in ethyl acetate solution (2 ml), was added under nitrogen atmosphere to the solution in which 5, 5, 6-trifluoro-6-(trifluoromethyl)bicyclo[2.2.1]hept-2-ene (28.22 g) and 1, 5-hexadiene (80 mg) were dissolved in ethyl acetate solution (60 ml), and was stirred at 50° C. Butylaldehyde (7 mg) was added 36 hours later, thereby the reaction being stopped. When measuring the reaction ratio of 0.1 g of the reaction solution by using ¹H-NMR, it was found that the polymerization reaction was driven to 100%. Another 1 g of the reaction solution was added into methanol to precipitate the ring-opening metathesis polymer, which was filtered and separated followed by being dried in a vacuum to obtain powder of the ring-opening metathesis polymer. The weight average molecular weight (Mw) of the ring-opening metathesis polymer measured by GPC was 49300, the molecular weight distribution (Mw/Mn) was 2.42, and Tg was 138° C.

Example 21

50.0 g of the reaction solution synthesized in Example 20 was subjected to a hydrogenation reaction with the use of palladium carbon at 160° C. and at a hydrogen pressure of 10 MPa. After that, the temperature was reduced to room temperature and hydrogen gas was discharged. The hydrogenated ring-opening metathesis polymer solution was added into methanol to obtain powder of the hydrogenated ring-opening metathesis polymer. The hydrogenation ratio of the polymer thus-obtained was 100%, the weight average molecular weight (Mw) was 53000, the molecular weight distribution (Mw/Mn) was 2.64, and Tg was 107° C.

Example 22

The solution in which Mo($=$CHCMe$_2$Ph)($=$N-2, 6-$^i$Pr$_2$C$_6$H$_3$)[OCMe(CF$_3$)$_2$]$_2$ (360 mg), which was synthesized in Example 2, was dissolved in THF solution (5 ml), was added under nitrogen to the solution in which 1,5-cyclooctadiene (5.22 g) was dissolved in THF solution (20 ml), and was stirred at room temperature. Butylaldehyde (120 mg) was added thereto 3 hours later, thereby the reaction being stopped. When measuring the reaction ratio of 0.1 g of the reaction solution by using $^1$H-NMR, it was found that the polymerization reaction was driven to 100%. Another 1 g of the reaction solution was added into methanol to precipitate the ring-opening metathesis polymer, which was filtered and separated followed by being dried in a vacuum to obtain powder of the ring-opening metathesis polymer. The weight average molecular weight (Mw) of the ring-opening metathesis polymer measured by GPC was 74300, the molecular weight distribution (Mw/Mn) was 1.54, and Tg was –100° C.

Example 23

The solution in which Mo($=$CHCMe$_2$Ph)($=$N-2, 6-$^i$Pr$_2$C$_6$H$_3$)[OCMe(CF$_3$)$_2$]$_2$ (40 mg), which was synthesized in Example 2, was dissolved in THF solution (2 ml), was added under nitrogen atmosphere to the solution in which 2, 3-bistrifluoro-7-oxa-bicyclo[2.2.1]hepta-2, 5-diene (7.4 g) was dissolved in THF solution (60 ml), and was stirred at room temperature. Butylaldehyde (15 mg) was added thereto 40 hours later, thereby the reaction being stopped. When measuring the reaction ratio of 0.1 g of the reaction solution by using $^1$H-NMR, it was found that the polymerization reaction was driven to 100%. Another 1 g of the reaction solution was added into methanol to precipitate the ring-opening metathesis polymer, which was filtered and separated followed by being dried in a vacuum to obtain powder of the ring-opening metathesis polymer. The weight average molecular weight (Mw) of the ring-opening metathesis polymer measured by GPC was 176000, the molecular weight distribution (Mw/Mn) was 1.13, and Tg was 91° C.

Example 24

50.0 g of the reaction solution synthesized in Example 23 was subjected to a hydrogenation reaction with the use of palladium carbon at 130° C. and at a hydrogen pressure of 9.5 MPa. After that, the temperature was reduced to room temperature and hydrogen gas was discharged. The hydrogenated ring-opening metathesis polymer solution was added into methanol to obtain powder of the hydrogenated ring-opening metathesis polymer. The polymer thus-obtained was hydrogenated to both double bonds in the main chain and within the cycle, and the hydrogenation ratio was 100%, the weight average molecular weight (Mw) was 190000, the molecular weight distribution (Mw/Mn) was 1.21, and Tg was 38° C.

Example 25

Mo($=$CHCMe$_2$Ph)($=$N-2, 6-$^i$Pr$_2$C$_6$H$_3$)(OSO$_2$CF$_3$)$_2$ (dme)(1.00 g) was placed in a 50 ml round bottomed flask under nitrogen and suspended in diethylether then was added with 0.33 g of pyridine (Py) at room temperature under stirring. Subsequently cooling to –30° C., 0.43 g of 2, 6-dichlorophenol(2, 6-Cl$_2$C$_6$H$_3$OH) was added under stirring. Removing the solvent 3 hours later then extracting with pentane, the mixture was filtered and evaporated to dryness in vacuo to obtain 0.46 g of yellow solid. NMR spectrum of the solid indicated that Mo($=$CHCMe$_2$Ph)($=$N-2, 6-$^i$Pr$_2$C$_6$H$_3$) (O-2, 6-Cl$_2$C$_6$H$_3$)$_2$(Py) was formed. No alkali metal was detected in the obtained solid.

The invention claimed is:

1. A process for producing (C) an organic transition metal complex compound, comprising:
converting an atom group having an electron-withdrawing ability of (A) an organic transition metal complex compound with an atom group having an electron-withdrawing ability, into an atom group having an electron-withdrawing ability derived from (B) a compound having a proton-donor ability, by contacting (B) said compound having a proton-donor ability with (A) said organic transition metal complex compound with an atom group having an electron-withdrawing ability, in the presence of a basic compound, wherein said compound having a proton-donor ability is at least one or more selected from an alcohol and a thiol.

2. The process for producing said organic transition metal complex compound as claimed in claim 1,
wherein (A) said organic transition metal complex compound with an atom group having an electron-withdrawing ability, has a metal alkylidene or a metal alkylidyne.

3. A process for producing a metathesis catalyst, wherein said process for producing an organic transition metal complex compound as claimed in claim 1 is used.

* * * * *